United States Patent [19]

Shapiro et al.

[11] Patent Number: 4,898,878
[45] Date of Patent: Feb. 6, 1990

[54] ANTIOXIDANT THIOHISTIDINE COMPOUNDS

[75] Inventors: Bennett M. Shapiro; Eric E. Turner; Paul B. Hopkins; Rachel E. Klevit; Tod P. Holler; Andreas Spaltenstein, all of Seattle, Wash.

[73] Assignee: The Board of Regents of the University of Washington, Seattle, Wash.

[21] Appl. No.: 104,736

[22] Filed: Oct. 2, 1987

[51] Int. Cl.$^4$ .......................... A61K 31/415
[52] U.S. Cl. .................... 514/386; 514/397; 514/398; 548/101; 548/103; 548/110; 548/112; 548/119; 548/301; 548/336; 548/337
[58] Field of Search ............ 548/337, 336, 101, 103, 548/110, 311, 112, 313, 119, 301; 514/184, 189, 397, 398, 386, 389, 390

[56] References Cited

PUBLICATIONS

Chemical Abstracts, 108:33971u (1988), [Turner, E., Diss. Abstr. Int. B 1987, 48(3) 748].
Turner, E., et al., The Journal of Biological Chemistry 260(24):13163–13171, 1985.
Turner, E., et al., The Journal of Biological Chemistry 261(28):13056–13063, 1986.
Spaltenstein, A., et al., The Journal of Organic Chemistry 52:2977–2979, 1987.
Ito, S. et al., J.C.S. Chem. Comm. pp. 1042–1043, 1976.
Ito, S., et al., Experientia 35(1):14–15, 1979.
Nardi, G., et al., Comp. Biochem. Physiol. 71B:297–300, 1982.
Palumbo, A., et al., Tetrahedron Letters 23(31):3207–3208, 1982.
Palumbo, A., et al., Comp. Biochem. Physiol. 7B(1):81–83, 1984.
Rossi, F., et al., Comp. Biochem. Physiol. 80B(4):843–845, 1985.
Turner, E., et al., Biochemistry 26:4028–4036, 1987.
Pathirana, C., et al., J. Am. Chem. Soc. 108:8288–8289, 1986.
Ito, S. et al., J.C.S. Perkin I, pp. 2617–2623, 1979.

Primary Examiner—Richard A. Schwartz
Attorney, Agent, or Firm—Christensen, O'Connor, Johnson & Kindness

[57] ABSTRACT

Therapeutic antioxidant compounds, useful for relieving the pathogenesis of oxidative stress, of formula

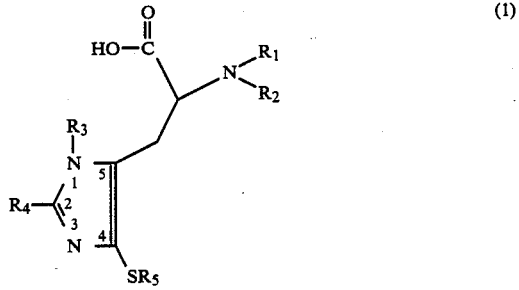

(1)

wherein substituents $R_1$, $R_2$, $R_3$, and $R_4$ are individually selected from among hydrogen, methyl, or other atoms and groups that do not adversely affect the overall spectrum of redox activity of the 4-thiohistidine. N-3 is unsubstituted or is substituted as described for $R_1$ to $R_4$. $R_6$ is preferably hydrogen or —SR.

4 Claims, 8 Drawing Sheets

ANTIOXIDANT THIOHISTIDINE COMPOUNDS

TECHNICAL FIELD

This invention relates to therapeutic antioxidant compounds useful for relieving the pathogenesis of oxidative stress.

BACKGROUND OF THE INVENTION

There is currently enormous interest in the dark side of oxygen, i.e., its capacity to cause disease. Hyperoxia is causal in disease processing such as retrolental fibroplasia and adult respiratory distress syndrome. Oxygen radicals formed under normoxic conditions have been implicated in diverse pathologies associated with inflammation, aging, drug toxicity, shock, reperfusion injury (i.e., that damage occurring after ischemia is relieved), radiation damage, and cancer. Oxidant damage is thought to be due to generation of partially reduced oxygen species such as superoxide ($O_2^-\cdot$) and hydrogen peroxide ($H_2O_2$) which give rise to more reactive species such as hydroxyl radical ($OH\cdot$), all of which cause damage to cellular components like nucleic acid, protein, lipids, and carbohydrate.

Although there is not unanimity on the pathogenic mechanism of $O_2$ toxicity, much current thinking implicates $O_2^-\cdot$ and $H_2O_2$, perhaps involving transition metals within the cell, in production of highly reactive radicals. For example, Fenton chemistry is part of an "iron-catalyzed Haber-Weiss reaction"

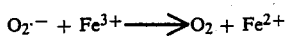  [1]

  [2]

that leads to the production of hydroxyl radical, so reactive that it attacks proximate molecules indiscriminately within a few molecular diameters. The net effect

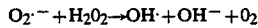

may be responsible for pathology. The question then becomes how partially reduced oxygen intermediates such as $O_2^-\cdot$ and $H_2O_2$ are or can be maintained at low enough intracellular levels to minimize such interactions and the resultant damage. One mechanism is to prevent their production. The primary cellular oxygen consumer, the respiratory chain, has cytochrome oxidase as the terminal electron acceptor which only releases oxygen upon its complete reduction to water. To remove reactive $O_2$ intermediates, catalases are present to deal with $H_2O_2$, especially when it is produced in or near peroxisomes. Glutathione peroxidase (see reaction [10], infra) acts as a major scavenging enzyme for cytosolic $H_2O_2$ and certain other hydroperoxides, with oxidized glutathione (GSSG) reduced by glutathione reductase (reaction [5], infra). Superoxide dismutase (SOD) exists in most aerobic cells to catalyze

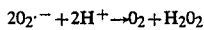  [4]

oxidation of superoxide. Much current effort implicates superoxide dismutase as a key protectant from oxidative stress, a hypothesis that has been supported by the discovery of mutants of E. coli and yeast that lack superoxide dismutase and have specific lesions in aerobic growth. Other cellular protecting agents such as thiols, vitamin E and ascorbic acid have less clearly defined roles.

The belief that oxygen radicals are responsible for disease has prompted attempts at therapy with superoxide dismutase and catalase in ischemia/reperfusion injury, inflammation, radiation injury and other disorders, with reports of success, although not all of the studies were carefully controlled and double blind in nature. The idea behind these approaches is that by interfering with the production of reactive oxygen species one could interfere with the pathophysiology. Despite its attractiveness, there are several difficulties with this approach, both conceptionally and practically. The pathogenesis of disease by oxidative stress and the exact role of different reduced $O_2$ species are not understood. Moreover, it is difficult to deliver proteins such as superoxide dismutase and catalase to the appropriate locus, and it is unlikely that they will reach the cytosolic compartment even when administered parenterally. Attempts have been made to produce low molecular weight superoxide dismutase analogues, such as Cu-salicylates or other chelated transition metals that might enter target cells and avoid the immunologic challenge posed by administering foreign proteins parenterally.

A principal reason that it has been difficult to unambiguously implicate reactive oxygen species in the pathogenesis of specific diseases is the absence of experimental models where the enzyme is actually present at the cellular target. Moreover, much of the suspect pathology occurs over a protacted period of time (e.g., in aging, carcinogenesis, etc.), so that linking slight modifications in reactive oxygen intermediates with disease is difficult.

SUMMARY OF THE INVENTION

Our interest in therapeutic antioxidant compounds was serendipitously generated by a biological problem and its apparent solution by nature. The sea urchin egg uses reactive oxygen intermediates for a key event, crosslinking the fertilization envelope. To do this, the evolutionary path of the sea urchin egg has provided a protective mechanism involving an amino acid derivative, which we call ovothiol, so that embryogenesis proceeds normally. Our observations suggest that unique biochemical properties of ovothiol allow it to detoxify reactive oxygen intermediates. This non-toxic (because it is present at 4 mM in early embryos) and low molecular weight (thereby giving it the capacity to enter cells and deal with reactive oxygen intermediates at their sites of generation) amino acid family may have therapeutic potential and should also be a powerful tool to investigate the role of reactive oxygen species in the pathogenesis of disease.

Thus, the invention provides redox active 4-thiohistidine ("ovothiol") derivatives of the formula

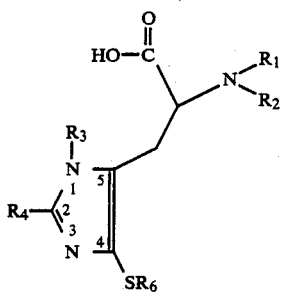

(1)

wherein substituents $R_1$, $R_2$, $R_3$, and $R_4$ are individually selected from among hydrogen, methyl, or other atoms and groups that do not adversely affect the overall spectrum of redox activity of the 4-thiohistidine. N-3 is unsubstituted or is substituted as described for $R_1$ to $R_4$. $R_6$ is preferably hydrogen or —S=O.

The amino acid moiety on the subject 4-thiohistidine compounds (1) is not required for imparting the requisite ovothiol-like redox activity. The invention therefore encompasses redox active 4-thioimidazole compounds of the formula

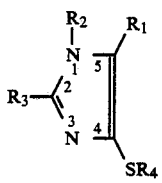

(2)

wherein the R substituents, a well as any substituent on N-3, are as stated generally above.

Furthermore, the C-4 positioning of the thiol on the imidazole in formulas 1 and 2 is critical for imparting the requisite redox activity to the subject compounds. The invention is therefore considered to encompass therapeutic antioxidant use of the following nonaromatic redox active thiol compounds

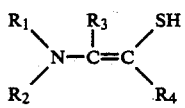

(3)

wherein the R substituents are as stated above, with $R_4$ preferably being —$NR_6R_7$.

Also provided is a method of regulating oxidative stress in an animal host by administering an effective amount of one or more (e.g., having different spectrums of redox activity) of the subject redox active compounds. Medicaments useful for regulating oxidative stress are thus provided, in the form of the subject redox active compounds in combination with printed or otherwise recorded instructions for administering the compound(s) to animal hosts for antioxidant effect.

DETAILED DESCRIPTION OF THE PREFERRED EMBODIMENT

Figure 1:
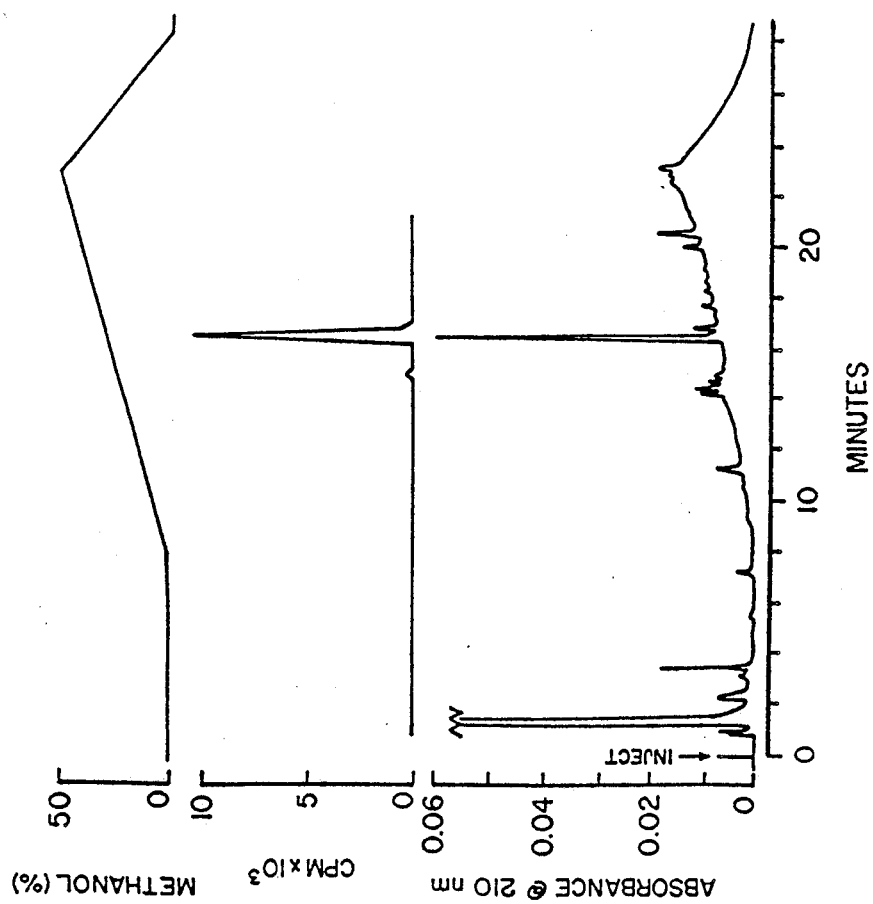
FIG. 1 presents data confirming the general screening protocol of Example 1 for identifying and isolating naturally occurring 4-thiohistidines such as ovothiol C.

Our previous studies of fertilization led us to propose a novel mechanism for detoxifying partially reduced ("reactive") oxygen intermediates, We will critically examine this mechanism, which surprisingly implicates aromatic thiols, such as the disclosed family of 4-mercaptohistidines, as cellular antoxidants. Before expanding upon the results that led us to this hypothesis, a brief excursion into the biology of fertilization is warranted.

Most animal eggs respond to fertilization by erecting a barrier that aids in the prevention of polyspermy (generally a lethal event) and protects the early embryo from deleterious environmental influences. The embryo later hatches from this shell to implant in the uterine wall (as with mammals) or become a free-living larval form (as with marine invertebrates). Some years ago we began a study of the envelope produced after sea urchin fertilization (reviewed in Kay, E., and B. M. Shapiro, Biology of Fertilization 3:45-80, 1985). The problem was interesting: sea urching eggs are fertilized in the ocean and within a few minutes form a extracellular coat that is resistant to degradation by proteases or protein denaturants. This extracellular biosynthesis takes place in the absence of cytosolic regulatory mechanisms and provides unique insights into morphogenetic control mechanisms.

The fertilizing sperm initiates a wave of calcium release from the endoplasmic reticulum of the egg, thereby eliciting exocytosis of some $10^4$ cortical vesicles to release about 5% of the egg protein. During the next 5 minutes released components catalytically and stoichiometrically interact with the egg glycocalyx to assemble a fertilization envelope. At this point $H_2O_2$ is synthesized in a burst that accounts for about 2/3 of the $O_2$ consumption of the "respiratory burst." The $H_2O_2$ is used as an oxidant to crosslink the assembled fertilization envelope with dityrosine residues (Foerder, C. A., and B. M. Shapiro, Proc. Nat. Acad. Sci U.S.A. 74:4214-4218, 1977: Kay, E. S., and B. M. Shapiro, Develop. Biol. 121:325-334, 1987), in a reaction catalyzed by a secreted ovoperoxidase (Deits, T., et al., J. Biol. Chem. 259:13525-13533, 1984), that is specifically inserted into the fertilization envelope by another secreted protein, proteoliaisin (Weidman, P., et al., J. Cell Biol. 100:938-946, 1984).

A serious potential problem emerges when an organism uses a deleterious oxidant like $H_2O_2$ as a key component of the physiological mechanism that initiates development. $H_2O_2$ and related oxygen radicals such as superoxide ($O_2^{-}\cdot$) and hydroxyl radical (OH·) pose a dramatic challenge to the cytosol and genome of the new embryo, yet somehow the fertilized sea urchin egg makes mM levels of $H_2O_2$ and survives. An additional point of interest in this regard is that seawater has a steady state

[H₂O₂] of 0.1 μM and [O₂·⁻] of 10 nM, with the potential of augmenting oxidative stress to the embryo. Thus, the sea urchin egg provides one of the few physiological models for the management of oxidant stress.

We have discovered that the sea urchin has evolved a system for dealing with this oxidative challenge that employs a redox active 4-mercaptohistidine of the ovothiol family. Our data suggest that ovothiol is a central feature of the protective mechanism, for the following reasons: (1) ovothiol is present in high concentrations in trotus purpuratus at the remarkably high concentration of 4 mM. It is specific as a cofactor for the CN⁻-resistant oxidase reaction and could not be replaced by other non-aromatic biological thiols such as glutathione, cysteine, Coenzyme A, or ergothioneine (5), the 2-thiolhistidine that is synthesized in fungi and found in many mammalian cells (and exists primarily in the thione forms; (Jocelyn, P. C., Biochemistry of the SH Group, Academic Press, N.Y. 1972; Melville, O., Vitam. Horm. 17:155–204, 1959).

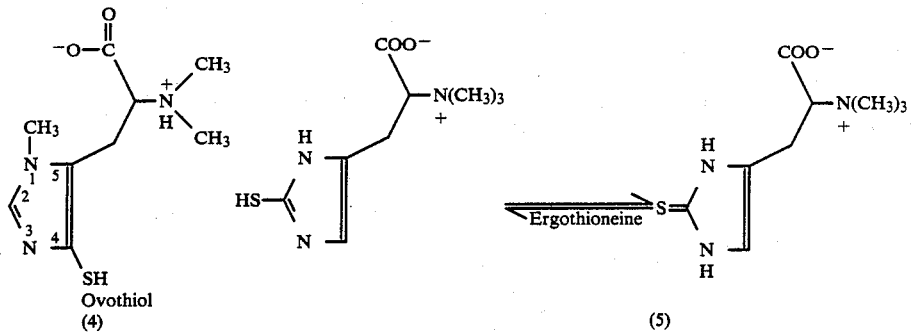

eggs and embryos; (2) ovothiol and glutathione account for glutathione peroxidase-like activity in eggs; (3) ovothiol is redox-active, and even in the absence of metal is several-fold more reactive than glutathione with H₂O₂; (4) at low [H₂O₂], the ovothiol system accounts for nearly all H₂O₂ consumption; (5) reaction of cellular ovothiol with the ovoperoxidase-ovidoreductase inhibitor iodoacetamide inhibits early development, and this effect is accentuated by addition of H₂O₂ and reversed by exogenous catalase; (6) ovothiol has a unique biochemical property in its capacity to act as a cofactor for the CN⁻-resistant NADH oxidation catalyzed by ovoperoxidase, for which only aromatic (and not aliphatic) thiols can substitute.

Our discovery of the redox active 4-mercaptohistidine family began with a search for the mechanism of H₂O₂ production of the CN⁻resistant respiratory burst of fertilization. Of several potential oxidases that were candidates for such a reaction, the NAD(P)H oxidase was particularly attractive, both because of the similarity to phagocytosis (Klebanoff, S. J., et al., J. Exp. M. 149:938–953, 1979; Badwey, J. A. and M. L. Karnosky, Ann. Rev. Biochem. 49:695–726, 1980; Babior, B., Trends in Biochem. Sci. 12:241–243, 1987), and because we had observed that both the pentose phosphate pathway and NAD kinase are activated at fertilization, with a net conversion of NAD to NADPH. A CN⁻-resistant oxidase was found at the egg surface that required a heat-stable egg cytosolic cofactor for activity (Turner E., et al., J. Biol. Chem. 260:13163–13171, 1985, hereby incorporated by reference). The enzyme responsible for this activity was purified and shown to be ovoperoxidase. That peroxidases could exhibit oxidase activity was known (Yamazaki, I., and K. Yokota, Molecul. Cell. Biochem. 15:39–52, 1973). The unusual feature of the ovoperoxidase-NAD(P)H oxidase was its relative CN³¹-insensitivity.

The heat-stable cofactor was purified to homogeneity and identified as 1-methyl-N⁶⁰, N^(α-dimethyl)-4-mercaptohistidine, or "ovothiol" (Turner E., et al., J. Biol. Chem. 261:13056–13063, 1986, hereby incorporated by reference) and termed ovothiol C (4) herein. Ovothiol (OSH) is present in eggs of the sea urchin Strongylocentrotus purpuratus at the remarkably high concentration of 4 mM. It is specific as a cofactor for the CN⁻-resistant oxidase reaction and could not be replaced by other non-aromatic biological thiols such as glutathione, cysteine, Coenzyme A, or ergothioneine (5), the 2-thiolhistidine that is synthesized in fungi and found in many mammalian cells (and exists primarily in the thione forms; (Jocelyn, P. C., Biochemistry of the SH Group, Academic Press, N.Y. 1972; Melville, O., Vitam. Horm. 17:155–204, 1959).

However, thiophenol and 1,5-dimethylimidazole-4-thiol (H3) were cofactors for the CN⁻-resistant oxidase, whereas N-acetyltyrosinamide was not. The oxidase is dependent upon Mn²⁺ and reduced ovothiol for maximal activity, with a K₀.₅ of 200 μM for ovothiol, with maximal activity at 1 mM. Mn²⁺ is optimal at 0.1–1 mM, with significant effect at μM Mn²⁺. The oxidase reaction is in the apparent requirement for partially reduced oxygen intermediates; it is inhibited by both superoxide dismutase and catalase. This CN⁻-resistant NAD(P)H oxidase of ovoperoxidase defines a unique property of aromatic thiols such as the 4-mercaptohistidines.

Although ovothiol is a specific cofactor for the CN⁻-insensitive ovoperoxidase-oxidase, several aspects of the biology and biochemistry of fertilization suggested that this is likely not its physiologic role. First, both ovothiol and NAD(P)H are intracellular metabolites, whereas ovoperoxidase is extracellular during the respiratory burst. The intracellular concentrations of NAD(P)H and ovothiol do not change significantly at fertilization, so neither is secreted to meet the ovoperoxidase. Second, H₂O₂ is not released stoichiometrically by the ovoperoxidase-oxidase, so this cannot account for the significant concentrations of H₂O₂ previously detected at fertilization. Third, aminotriazole inhibits both the NAD(P)H oxidase and peroxidase activities of ovoperoxidase, yet has no effect on oxygen consumption by eggs. Finally, derivatization of over 80% of egg ovothiol with iodacetamide does not block the H₂O₂-dependent fertilization envelope crosslinking. These data indicate that the ovothiol dependent NAD(P)H oxidase activity of ovoperoxidase is not involved in H₂O₂ production of the respiratory burst of fertilization.

We have subsequently discovered other 4-mercaptohistidines, called ovothiol A and B, in marine invertebrate eggs. Ovothiols A, B, and C differ in the extent of N^α methylation, but have identical redox properties.

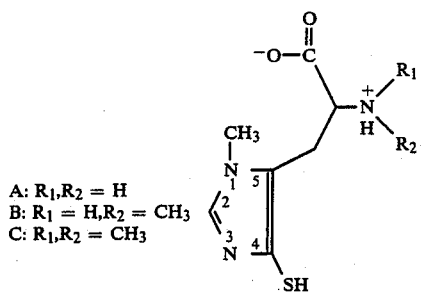

A: $R_1, R_2 = H$
B: $R_1 = H, R_2 = CH_3$
C: $R_1, R_2 = CH_3$

Such amino acids were also isolated by Palumbo and colleagues (see Example 3), but the substitution on the imidazole ring was misassigned, as shown by careful structural analysis and organic synthesis. Furthermore, Palumbo et al. did not recognize the special redox properties of the ovothiol family.

As disclosed in Example 1, we developed a sensitive radiochemical assay for ovothiol based on alkylation with [$^3$H]-iodoacetic acid and separation by HPLC, and used this assay to identify ovothiol in other species. Representative of the species distributions are ovothiol C (1-methyl-N$^\alpha$, N$^\alpha$-dimethyl-4-thiolhistidine) in the sea urchin *S. purpuratus*, ovothiol B (1-methyl-N$^\alpha$-methyl-4-thiolhistidine) in the scallop *Chlamys hastata*, and ovothiol A (1-methyl-4-thiolhistidine) in the starfish *Evasteria troschelii*. The ovothiols were primarily found in ovaries and not somatic tissue or sperm. So far, ovothiols have been detected in echinoids, asteroids, molluscs, ascidians, annelids, and in fish eggs.

We believe that ovothiol is present at mM levels in eggs undergoing the respiratory burst of fertilization in order to protect them from damage by reactive oxygen intermediates. This hypothesis is based in part on the data that is presented in some detail below.

The redox potential of ovothiol was determined, as were the kinetics for its interaction with glutathione and H$_2$O$_2$. The mid-point potential (E$^{o'}$) was estimated indirectly by determining the equilibrium in reaction with other known thiol-disulfide equilibria, since direct determination of (E$^{o'}$) for thiols is typically complicated by artifacts. Ovothiol exhibits distinct spectral changes on oxidation and reduction (J. Biol. Chem. 261:3056–13063, 1986), so measurement of the relative amounts of the two forms was facilitated. Appropriate corrections were made for the mixed disulfides present at different concentrations of ovothiol and glutathione. E$^{o'}$ (30°) for ovothiol was 44 mV positive relative to glutathione, or $-0.196$ V. Thus, the $\Delta G^{o'}$ for the reduction of ovothiol disulfide (OSSO) by reduced glutathione (GSH) is $-0.386$ kcal, so that at equilibrium reduced ovothiol (OSH) predominates in a mixture of equimolar oxidized ovothiol (OSSO) and reduced glutathione (GSH). From a thermodynamic point of view, ovothiol can be maintained almost entirely in the reduced state by GSH, and thus by NADPH via glutathione reductase, without the need for a specific ovothiol reductase. Since glutathione is over 90% reduced in sea urchin eggs and its redox state doe not vary significantly with the cell cycle, ovothiol would be found intracellularly as reduced ovothiol (OSH), as shown in the equations below.

$$GSSG + NADPH + H^+ \xrightarrow{\text{glutathione reductase}} 2GSH + NADP^+ \quad [5]$$

$$2GSH + OSSO \longrightarrow 2OSH + GSSG \quad [6]$$

$$\text{Sum: } OSSO + NADPH + H^+ \longrightarrow 2OSH + NADP^+ \quad [7]$$

Eggs contain high glutathione reductase activity (20-fold higher than erythrocytes). Because reduced glutathione reduces ovothiol, a functional ovothiol reductase reaction [7] exists by coupling reactions [5] and [6]. The second order rate constant for ovothiol reduction by glutathione is 88M$^{-1}$S$^{-1}$. We calculate that egg glutathione reductase is sufficient to produce 4.1 pmol GSH/min; with an egg GSH content of 0.9 pmol, it would take only 13 seconds for the egg to regenerate its entire GSH content from GSSG, if NADPH were present (which it is after fertilization). In the presence of normal cellular GSH levels, the t$_{1/2}$ for reduction of OSSO to OSH is 1.6 s. In other words, reduction of ovothiol is rapid at the concentrations of glutathione and ovothiol of the egg, and an enzymatic "ovothiol reductase" is not required to catalyze reaction [7].

The non-enzymic reaction of OSH and H$_2$O$_2$ was measured and compared with GSH reacting with H$_2$O$_2$. For reaction [8] the second order rate constant was 3.3M$^{-1}$S$^{-1}$ determined by spectrophotometric assay. Measurement of reaction [9] by coupling to glutathione reductase gave a K=1.5M$^{-1}$S$^{-1}$.

$$2OSH + H_2O_2 \rightarrow OSSO + 2H_2O \quad [8]$$

$$2GSH + H_2O_2 \rightarrow GSSG + 2H_2O \quad [9]$$

Since a single egg produces 0.5 pmol of H$_2$O$_2$ during the 20 min of the respiratory burst, this represents production of 100 μM H$_2$O$_2$/min averaged over the intracellular volume. Non-enzymatic destruction of H$_2$O$_2$ by reaction with OSH may play a significant role in controlling its toxicity, by coupling reactions [6] and [8] as shown below.

$$2GSH + OSSO \rightarrow 2OSH + GSSG \quad [6]$$

$$2OSH + H_2O_2 \rightarrow OSSO + 2H_2O \quad [8]$$

$$\text{Sum: } 2GSH + H_2O_2 \rightarrow GSSG + H_2O \quad [10]$$

Thus, ovothiol provides the egg a functional, non-enzymatic glutathione peroxidase mechanism, e.g., reaction [10], to dissipate H$_2$O$_2$. Glutathione peroxidase (GSH Px) is coupled to glutathione reductase in mammalian cells (Meister, A., and M. E. Anderson, Ann. Rev. Biochem. 52:711–760, 1983; Stadtman, T. C., Meth. in Enzymol. 107:576–581, 1984), and in eggs an analogous situation could obtain. Although the reaction of ovothiol with H$_2$O$_2$ is slow compared to glutathione peroxidase, sea urchin eggs appear to lack the heat-labile, selenium dependent glutathione peroxidase, as shown in Table I.

TABLE I

| Sample | Glutathione peroxidase (mU/mg) | |
|---|---|---|
| | intact | boiled |
| Egg homogenate | 1.8 | 1.6 |
| Equivalent amount OSH and GSH | 1.6 | 1.6 |

TABLE I-continued

| Sample | Glutathione peroxidase (mU/mg) | |
|---|---|---|
| | intact | boiled |
| Erythrocyte lysate | 18.1 | <0.5 |

When egg homogenates were assayed for glutathione peroxidase, all of the activity was heat stable in contrast to the classic selenium-dependent enzyme of mammalian cells. The activity was within 20% of that accounted for by the OSH and GSH concentration of eggs (4.3 mM and 3.4 mM, respectively). These data suggest that there is little or no enzymatic glutathione peroxidase in eggs, but that the OSH and GSH replace it.

The following biological experiment further implicates ovothiol in protection of eggs from $H_2O_2$ produced during the respiratory burst. If ovothiol were important in protection, then its absence should lead to embryonic lethality. Egg thiol modification blocks sea urchin development (Nath, J., and L. I. Rebhun, J. Cell Biol 68:440-450, 1976), and we demonstrated that modification of ovothiol with iodoacetamide (IAA) in intact eggs led to inhibition of cellular division. However, iodoacetamide might have reacted with critical proteins (or other components) required for cell division, so that experiment was not definitive in implicating ovothiol. More recently, we added exogeneous catalase to eggs derivatized with iodoacetamide. Catalase should act as a second mechanism for removing $H_2O_2$ and partially compensate for the iodoacetamide treatment. The first cell division was blocked for eggs treated with 1.0 mM iodoacetamide prior to the respiratory burst (7% cleavage vs. 90% of control eggs). With catalase present during the respiratory burst, 70% of IAA-treated eggs divided (and 90% of the controls). Pretreatment with 0.25 mM iodoacetamide decreased cleavage to 75%; with exogenous 0.1 mM $H_2O_2$ added, cell division occurred in only 2% of these eggs, and with catalase present in 90%. Control eggs (not treated with iodoacetamide) were unaffected by 0.1 mM $H_2O_2$.

Another interesting observation concerns the ability of sea urchin eggs to destroy exogenously added $H_2O_2$. After addition of $H_2O_2$, its rate of disappearance was estimated (by using the fluorescent scopoletin assay, as in Foerder, C. A., et al., Proc. Nat. Acad. Sci USA 75:3183-3187, 1978) for intact eggs treated with iodoacetamide (to derivatize ovothiol, and some glutathione) and eggs treated with $N_3^-$ (to inhibit catalase). Eggs used both the catalasedependent and OSH/GSH-dependent mechanisms to destroy $H_2O_2$: the latter was the predominant system at the low steady state $H_2O_2$ levels characteristic of the respiratory burst. These results additionally support the relevance of ovothiol in protecting the early embryo from oxidative stress.

In summary, our studies on sea urchin fertilization have unearthed a novel redox active amino acid, the 4-mercaptohistidine ovothiol family, that is implicated as a cellular antioxant. Ovothiol has unusual, and in some cases, unique properties. Ovothiols are present in eggs and ovaries of marine invertebrates and fish and are capable of reducing $H_2O_2$. This amino acid has potential utility as an exogenously supplied antioxidant reagent in other cells, including human and other mammalian cells, as well.

Thus, the invention provides redox active 4-thiohistidine compounds of the formula

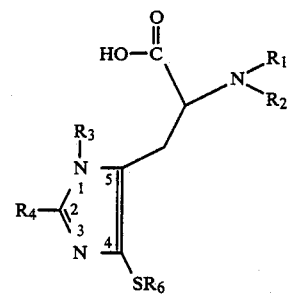

(1)

wherein the substituents (R) can be individually selected from among hydrogen and methyl. Of course, other R groups are not only permissible but may contribute to the redox activity, $pK_a$, transport capability, and atoxicity of the subject compounds, for therapeutic effect. Thus, representative $R_1$ and $R_2$ substituents on the $\alpha N$ include hydrogen, alkyl, halogen, carboxylate, nitrile, alcohol, amine, and aldehyde. By alkyl is meant straight or branch chain alkyl groups of from 1 to about 22 carbon atoms, the lower alkyls of 1 about 5 carbon atoms affording solubility in aqueous solution, and the higher alkyls of from about 6 to 22 carbon atoms affording lipid solubility to the subject compounds. By halogen is meant —F, —Cl, —Br, —I, and —At. An alkyl group (hereinafter referred to as "A") in $R_1$ and/or $R_2$ can be bonded directly to $\alpha N$, or a heteroatom or group can intervene. Thus, $R_1$ and $R_2$ can be: organophosphorus such as 13 $PR_1R_2$, —$P(O)R_1R_2$, and —$P(O)(OR_1)(OR_2)$; organoselenium such as —SeA, —Se(O)A, and —Se(O)$_2$A; organosulfur such as —SA, —S(O)A, and —S(O)$_2$A; carboxylic ester —$CO_2R$; amine —C(=NA$_1$)NA$_2$A$_3$; ether —OA; hydrazine or amine —NAA; aldehyde —C(O)A; organosilicon —SiA$_1$A$_2$A$_3$; organoboron —BA$_1$A$_2$A$_3$; organotellurium such as —TeA, —Te(O)A, and —Te(O)$_2$A; organotin —SnA$_1$A$_2$A$_3$; and organothallium —TlA. The heteroatom or above-listed group can likewise replace one or more —$CH_2$— group in alkyl A; similarly, —CH=CH— or —C≡C— can replace one or more —$CH_2CH_2$— groups in constituent "A".

$R_1$ or $R_2$ can also include a divalent group such as thiol, —SH, (typically separated from $\alpha N$ by an alkyl or other spacer) capable of permanently or transiently interacting covalently or noncovalently with the sulfur atom on C-4, resulting in modification of the redox activity as a mechanism of fine tuning the antioxidant activity of the molecule for therapeutic effect.

Substituent $R_3$ need not be methyl (as in the naturally derived ovothiols that have been isolated to date); nor must $R_4$ be hydrogen. Thus, $R_3$ on N-1 and $R_4$ on C-2 can be selected within the functional constraints set forth above from any of the atoms or groups listed for $R_1$ or $R_2$. N-3 can be either unsubstituted or substituted with any of the atoms or groups listed above for $R_1$ and $R_2$. Such substituents $R_3$, $R_4$, and particularly any substituent on N-3, may change the redox properties of the thiol, possibly fine tuning therapeutic utility.

The subject compounds must bear —SH on C-4 in the intracellular environment, for antioxidant effect, but as medicines can be supplied in redoxinactive forms. That is, C-4 can bear —$SR_6$, wherein —$SR_6$ is preferably a disulfide and most preferably the symmetrical disulfide. Alternatively, $R_6$ is selected from among the atoms and groups listed above for $R_1$ and $R_2$, selected along solubility, transport (drug delivery), toxicity, and $pK_a$ criteria, and furthermore for being metabolizable or otherwise convertible from $-SR_6$ to $-SH$ within the animal host and particularly intracellularly.

Also provided is a method of regulating oxidative stress in an animal host by administering an effective amount of one or more (e.g., having different spectra of redox activity) of the subject redox active compounds. Medicaments useful for regulating oxidative stress are thus provided, in the form of the subject redox active compounds in combination with printed or otherwise recorded instructions for administering the compounds(s) to animal hosts for antioxidant effect. The subject compounds are preferably formulated and administered in their L-configuration, for enhancement of cellular uptake.

The amino acid moiety on the subject 4-thiohistidine compounds (1) is not required for imparting the requisite ovothiol-like redox activity. The invention therefore also encompasses redox active 4-thioimidazole compounds of the formula

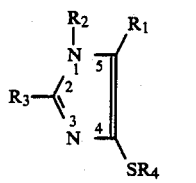

(2)

wherein the stated R substituents, as well as any optional substituents on N-3, may be selected from the atoms and groups listed above for formula 1, subject to the same functional constraints with particular attention here to selecting substituents that will impart atoxicity in animal, particularly mammalian, cells.

Furthermore, the C-4 positioning of the thiol on the imidazole in formulas 1 and 2 is critical for imparting the requisite redox activity to the subject compounds. The invention is therefore considered to encompass therapeutic antioxidant use of the following nonaromatic redox active thiol compounds

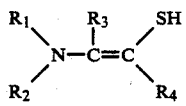

(3)

wherein $R_1$, $R_2$, $R_3$, and $R_4$ are as defined above, with $R_4$ preferably being $-NR_1R_2$.

The compounds of this invention have been found to possess unusual and potentially valuable pharmacological properties. Due to their redox activity, small size, and lack to toxicity, the subject compounds may exhibit an antioxidant effect in human and veterinary medicine. This valuable antioxidant effect can be demonstrated, for example, using the protocols set forth in the Examples.

Thus, the subject compounds can be administered to a mammal to relieve oxidative stress associated with diverse pathologies such as inflammation, aging, drug toxicity, ischemic/reperfusion injury, shock, radiation damage, and cancer. The compounds are considered to be particularly useful as oral antioxidant compounds.

In addition, the subject compounds can be as intermediates in the production of other antioxidant drugs, e.g., by the representative protocols set forth in the Examples.

The compounds of this invention are generally administered to animals, including but not limited to mammals, birds, and fish, and especially to humans, livestock, and household pets.

The pharmacologically active compounds of this invention can be processed in accordance with conventional methods of galenic pharmacy to produce medicinal agents for administration to human, patients and other animals hosts.

The compounds of this invention can be employed in admixture with conventional excipients, i.e., pharmaceutically acceptable organic or inorganic carrier substances suitable for enteral (e.g., oral), patenteral, or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, perservatives, stabilizers, wetting agents, emulsifiers, salts for influencing osmotic pressure, buffers, coloring, flavoring and/or aromatic substances and the like which do not deleteriously react with the active compounds. They can also be combined where desired with other therapeutic agents, e.g., vitamins.

For enteral application, particularly suitable are tablets, dragees, liquids, drops, suppositories, or capsules. A syrup, elixir, or the like can be used wherein a sweetened vehicle is employed.

For parenteral application, particularly suitable are injectable, sterile solutions, preferably oily or aqueous solutions, as well as suspensions, emulsions, or implants, including suppositories. Ampoules are convenient unit dosages.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilizates obtained, for example, for the preparation of products for injection.

For topical application, there are employed as nonsprayable forms, viscous to semi-solid or solid forms comprising a carrier compatible with topical application and having dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

Oral administration is preferred, since the subject amino acid derivatives should be resistant to degradation in the gastrointestinal tract and therefore available in the bloodstream for accumulation by cells at the site(s) of oxidative damage. These therapeutic compounds are preferably administered to the animal host in the oxidized, disulfide form; they are reduced intracellularly to act as intracellular antioxidants. Since the natural ovothiols exist at extraordinarily high concentrations in viable cells, dosage-dependent toxicity is not considered to present a significant problem in the subject therapy.

It will be appreciated that the dosage of the compounds according to this invention in any specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of appropriate, conventional pharmacological protocols in light of the Examples set forth below.

The invention is further described by means of the following Examples. Example 1 presents a general screening protocol that can be used to identify and isolate naturally occurring 4-thiohistidines. Examples 2 and 3 set forth a general protocol for synthesizing 4-thiohistidine derivatives like the naturally occurring ovothiols as well as their synthetic analogues. In Example 4, a general synthesis route for achieving the subject 4-thioimidazoles is presented. The next three Examples disclose representative screening protocols for assaying the isolated or synthesized aromatic thiol compounds for redox activity. Example 5 presents a variety of preliminary assays for reaction with oxygen radicals. Example 6 presents an optional set of intermediate screening protocols for assaying protection of macromolecules from oxidative damage. Example 7 presents a series of alternative protocols that can be used to assay for inhibition of the cellular damage caused by oxidative stress. Finally, in Example 8, a putative mammalian analog of ovothiol is disclosed, along with protocols for its isolation, characterization, and testing.

EXAMPLE 1

Identification and isolation of ovothiol compounds

Here we report a useful new method for isolation and identification of naturally occurring 4-thiohistidines by ion-pairing high performance liquid chromatography (HPLC), following S-carboxymethylation with iodoacetic acid. As representative embodiments, this technique was used to identify two novel thiohistidine compounds from starfish and scallop which differ from the previously reported $S.$ $purpuratus$ compound (1-methyl-$\alpha$N,$\alpha$N-dimethyl-4-thiohistidine) in the extent of a $\alpha$-N methylation.

Materials and methods

Nicotinamide adenine dinucleotide (NADH), dithionitrobenzoic acid (DTNB), dithiothreitol, amiotriazole, iodoacetic acid, iodoacetamide, glutathione reductase, reduced gluthathione (GSH), oxidized gluthathione (GSSG), 1-methylhistidine, 3-methylhistidine, and Dowex resin were obtained from Sigma. $D_2O$ (99.96% D) was obtained from KOR Isotopes. $^3$H-iodoacetic acid and $^{14}$C-iodoacetamide were reagent grade or the highest grade commercially obtainable.

Specimens of $S.$ $purpuratus$ were gathered intertidally in the Strait of Juan de Fuca. Animals were spawned by intracoelomic injection of 0.5M KCl. Other tissues were obtained by dissection of fresh animals; gut tissue was obtained from animals fasted approximately 30 days. For embryo culture, $2.8 \times 10^7$ eggs (50 ml) were fertilized with $5 \times 10^9$ sperm in 2 liters Millipore-filtered sea water (MFSW). After 30 minutes, eggs were allowed to settle, and excess sperm were decanted. Embryos were then resuspended with gentle stirring and aeration in 20 liters MFSW containing 0.2 mM ethylenediaminetetraacetic acid (EDTA). Embryos were harvested by low speed centrifugation at appropriate time points and immediately frozen at $-80°$ C. Specimans of the bay scallop Chlamys hastata were caught off the coast of Vancouver Island and purchased alive from a local source, and Evasterias troschelii were collected intertidally from Puget Sound. Tissues were dissected from fresh specimens with care to avoid contamination with gonadal material.

NAD(P)H—$O_2$ oxidoreductase activity was measured by following the oxidation of reduced pyridine nucleotides spectrophotometrically at 360 nm in a Gilford 420 spectrophotometer. The off-peak wavelength of 360 nm for reduced pyridine nucleotides allowed the use of higher concentrations in a 1.0 cm pathlength cuvette. Assays were conducted in a 1 ml volume containing 50 mM NaCl, 20mM Hepes, 20 mM Tris, at pH 8.0 and 25° C., to which was added for routine assays 0.4 mM NADH, 0.5 mM $MnCl_2$, 1 mM NaCN, 134 nM ovoperoxidase, and the appropriate amount of ovothiol preparation. One unit of activity is defined as the amount of ovothiol needed to stimulate consumption of 1.0 nanomoles NADH/min. The dissolved $O_2$ concetration of the buffer system at 20° C. was 305 $\mu$M. Assays were initiated with NADH unless otherwise specified. Ovothiol A and C disulfide were quantitatively reduced for enzymatic studies by incubation for 10 min with a twofold molar excess of dithiothreitol, followed by separation on Dowex-50$\times$8 ion exchange resin, $NH_4^+$-form, under $N_2$ as described in Turner et al., J. Biol. Chem. 260:13163–13171, 1986 (hereinafter, "Turner et al., 1986").

Glutathione assays were done by a modification of the glutathione reductase method of Griffith (Anal. Biochem. 106:207–212, 1980) for total GSH plus GSSG. Sample or standard was added to a cuvette containing 100 mM sodium phosphate, 5 mM EDTA, 0.21 mM NADPH, 0.6 mM DTNB, and 0.5 units of glutathione reductase at pH 7.5 and 30° C. in a final volume of 1 ml. Change in $A_{412}$ due to the formation of 5-thio-2-nitrobenzoic acid was monitored and the rate of change between 1.0 and 2.0 OD calculated; optimal rates were obtained with 0.5-5 nmol GSH. Samples were prepared by incubation of tissue homogenate with 0.2 mM DTT for 10 min to reduce mixed disulfides, followed by addition of 100% trichloroacetic acid to 5% final concentration and centrifugation in a microfuge for 3 min. Up to 50 $\mu$l of supernatant could be used in the assay without significantly lowering the pH. Internal and external standards of GSH were used to produce a standard curve for each set of assays; GSSG gave identical results. Inclusion of DTT in the sample preparation had no effect on the standard curve. Ovothiol did not react in the glutathione assay and did not interfere with the assay of glutathione standards when added at equimolar concentration.

NMR Spectroscopy. Proton NMR spectra were obtained at 500 MHz on a Bruker WM-500. All spectra were collected at ambient temperature. Specific acquisition parameters used are discussed below. All chemical shifts were measured relative to an external standard of sodium 4,4-dimethyl-4-silapentane-1-sulfonate (DSS). Des-S-ovothiol A was prepared by the Raney nickel method described for ovothiol C (Turner et al., 1986).

High pressure liquid chromatography. All HPLC was performed on a Beckman model 334 liquid chromatopgraph. Ion-exchange HPLC was performed as described (Turner et al., 1986) with a Waters protein-pak SP-5PW column; a 30 cm Waters Bondapak C-18 column preceded the ion-exchange column and served to desalt the sample and provide adequate back pressure at a flow rate of 1.0 ml/min. Chromatograms were developed with a linear gradient of 0.05 to 2.0M ammonium formate, pH 2.5 (2.0M formic acid, adjusted to appropriate pH with ammonium hydroxide).

Ion-pairing HPLC utilized a 15 cm Altex ultrasphere-ODS C-18 column and standard precolumn (Beckman). Chromatograms were developed using a linear gradient of 0-50% methanol in a buffer system containing 20 mM phosphoric acid and 5 mM sodium heptane sulfonate, adjusted to pH 2.5 with ammonium hydroxide, at a flow rate of 1.6 ml/min.

Scintillation counting was performed in a Beckman LS-230 liquid scintillation counter. Samples in aqueous solution were mixed with $H_2O$ to a total volume of 0.5 ml, followed by 8 ml of Aquasol. Counting efficiency for tritium in this system was 50%.

Assay of ovothiols by S-carboxymethylation and preparation of standards

Ovothiol A, B, and C were detected quantitatively by treating tissue homogenates with $^3H$-iodoacetic acid, followed by isolation of the S-carboxymethyl derivatives of the ovothiols by Dowex-50 ion exchange chromatography and HPLC. For routine assays, tissues were homogenized with 4 volumes of $H_2O$ in a Virtis 45 tissue homogenizer and/or Teflon pestle homogenizer. One ml of tissue homogenate was adjusted to pH 8, mixed with 1 $\mu$mol of DTT, incubated 10 minutes, then mixed with 2.5 $\mu$mol of $^3H$-iodoacetic acid containing $2 \times 10^6$ cpm tritium/$\mu$mol. For tissues such as egg and ovary which are especially rich in ovothiol, 0.25 ml of 20% homogenate was diluted to 1 ml before derivatization. After a 30 minute incubation, samples were precipitated with 10% trichloroacetic acid and protein was pelleted by microcentrifugation for 3 minutes. The supernatant solution was applied to a disposable plastic column (Kontes) containing 1.0 ml packed bed volume of Dowex-50$\times$8 100-200 mesh, ammonium form. The column was preequilibrated in 0.5M formic acid and washed with 10 ml of the same following sample application. The bound ovothiol was eluted with 10 ml of 0.5M ammonium formate, pH 4.5 (0.5M in $NH_4^+$, adjusted to pH 4.5 with formic acid, 88%), the eluant twice lyophilized from $H_2O$, then redissolved in $H_2O$ and applied to the ion-pairing or ion exchange HPLC systems described above. Samples were mixed with 0.2 volumes of 1M phosphoric acid/0.25M sodium heptane sulfonate and adjusted to pH 2.5 with 6N HCl prior to ion-pairing HPLC; the pH only was adjusted to the same value prior to ion exchange HPLC. The isolation procedure consistently gave >90% recovery of ovothiol added prior to derivatization.

Standards of $^3H$-S-carboxymethyl ovothiol A and B were prepared essentially by scaling up the procedure above. For ovothiol B, 30 g of *Chlamys hastata* ovarian tissue containing 2.3 g of protein were thoroughly homogenized with $H_2O$ to a total volume of 120 ml, and boiled 10 min on a water bath. The protein precipitate was removed by centrifugation (25,000 g) for 30 min and 75 ml of the clear superatant was treated with 0.4 mM dithiothreitol for 10 min, followed by 2.5 mM $^3H$-iodoacetic acid containing $1 \times 10^6$ cpm/$\mu$mol tritium for 30 minutes. The sample was then acidified with 5% trichloroacetic acid and applied to a column containing 30 ml packed bed volume of Dowex-50$\times$8, 200-400 mesh, ammonium form, preequilibrated with 0.5M formic acid. The column was washed with 300 ml 0.1M formic acid and eluted in batch with 0.5M ammonium formate pH 4.5. Fractions of 1 ml containing $\leq$100,000 cpm were pooled and twice lyophilized from $H_2O$. The eluant was redissolved in 1 ml, and aliquots of 150 $\mu$l were applied to ion exchange HPLC as described above. The principal peaks of eluted radioactive material from several separations were pooled and relyophilized. Yield was approximately 4 $\mu$mols S-carboxymethyl ovothiol B. The identity of the material was confirmed by $^1H$-NMR as described below. An essentially identical procedure applied to the ripe gonads of the starfish *Evasterias troschelii* yielded a preparation of homogeneous S-carboxymethyl ovothiol A.

S-carboxymethyl ovothiol C was prepared from material isolated in the underivatized disulfide form by solvent extraction, ion exchange chromatography and HPLC as previously described (Turner et al., 1986). 10 $\mu$mols of ovothiol C disulfide were incubated with 30 $\mu$mols dithiothreitol in 0.2 ml 100 mM sodium bicarbonate for 20 minutes; subsequently 0.1 ml of 1M $^3H$-iodoacetic acid, $5 \times 10^5$ cpm/$\mu$mol, was added. After 30 minutes the mixture was acidified with 10% trichloroacetic acid and applied to 2 ml Dowex-50$\times$8, 100-200 mesh, ammonium form, which had been pre-equilibrated in 0.5M formic acid. The column was washed with 10 ml of 0.5M formic acid and the $^3H$-S-carboxymethyl ovothiol C eluted with 10 ml of 0.5M ammonium formate, pH 4.5 (0.5M in ammonium ion). Yield approached 100% (20 $\mu$mols) of the expected amount of product.

Isolation of S-carboxymethyl ovothiol A, B, and C and separation of standards.

FIG. 1 shows the isolation of S-carboxymethyl ovothiol C from *S. purpuratus* egg homogenate by ion-pairing HPLC following iodoacetic acid derivatization and Dowex-50 chromatography as described above. S-carboxymethyl ovothiol C accounts for the principal peak of radioactivity and UV absorbance eluted from the column. The trace represents an extract of approximately $5 \times 10^3$ eggs.

Figure 2:
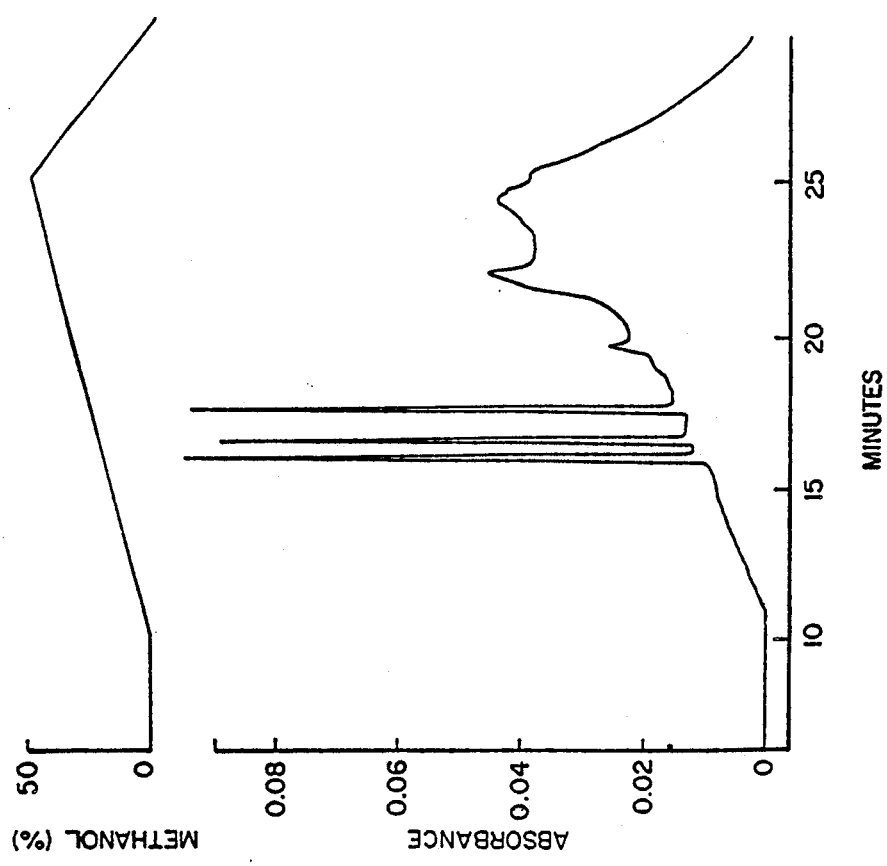
FIG. 2 presents comparative data demonstrating the isolation of three representative 4-thiohistidines (ovothiols A, B, and C) from natural sources, as described in Example 1.

FIG. 2 shows ion-pairing HPLC separation of 2.0 nmol each of S-carboxymethyl ovothiol A, B, and C standards (applied in a total volume of 20 $\mu$l) prepared as described above. Baseline resolution of the three methylation forms is achieved, with the elution order of ovothiol C, B, A.

Underivatized ovothiol A disulfide was isolated as previously described for ovothiol C (Turner et al., 1986), with the exception that the final step of ion-exchange HPLC was replaced by repeat chromatography on Dowex-50, giving a product which showed only trace organic impurities on $^1H$-NMR. As with ovothiol C, air oxidation of the compound to the disulfide form during the purification was essentially complete. The disulfide was then reduced for enzymatic studies of its activity as an oxidase cofactor by treatment with dithiothreitol followed by Dowex-50 chromatography under $N_2$ as previously described (Turner et al., 1986). The oxidized and reduced ultraviolet spectra of ovothiol A showed characteristic differences similar to those previously reported for ovothiol C.

Structural Identification

Figure 3:
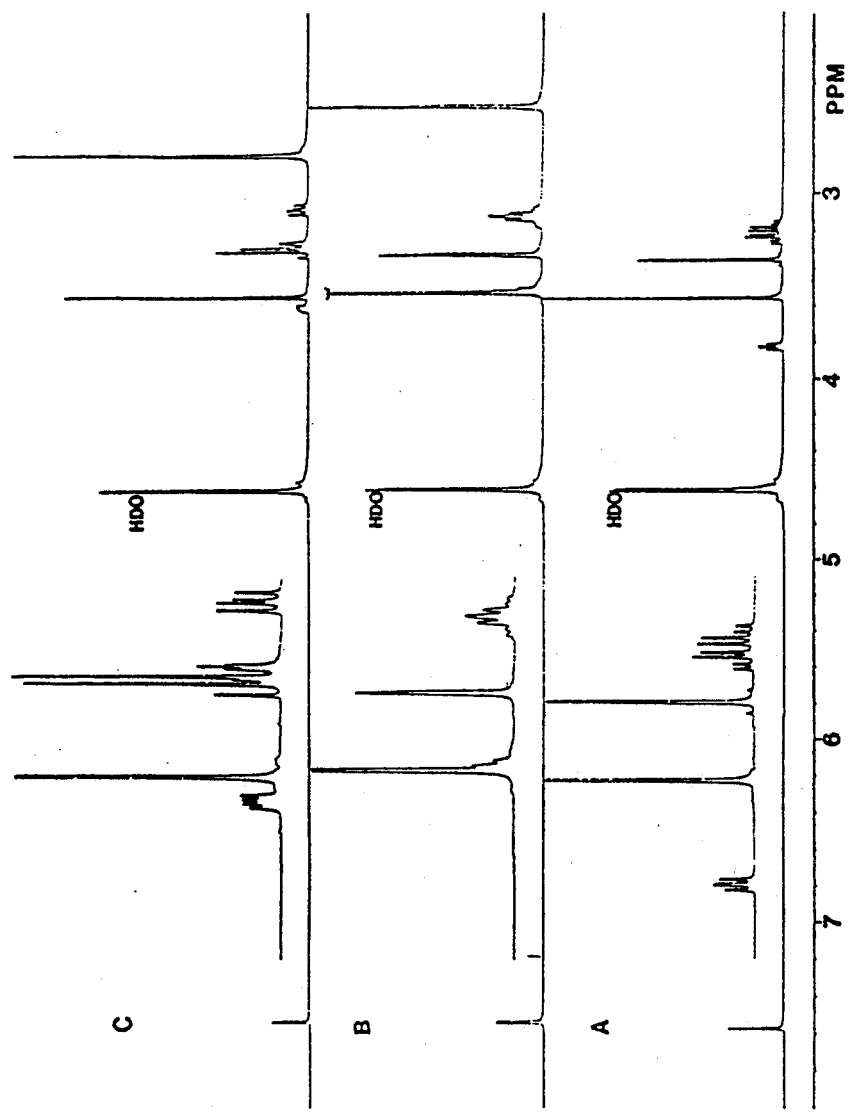
FIG. 3 presents comparative data demonstrating the structural identification of representative 4-thiohistidines, as described in Example 1.

The structure of ovothiol C has been previously elucidated by UV spectrophotometry, mass spectroscopy, and $^{13}C$ and $^{1}H$ NMR, including comparison by $^{1}H$-NMR of des-S-ovothiol C with commercially obtained 1-methyl and 3-methyl-αN,αN-dimethyl histidine (Turner et al., 1986). Nuclear Overhauser effect (NOE) studies also confirmed the N-1 position as the site of imidazole ring methylation. FIG. 3 shows the 500 MHZ $^{1}H$-NMR spectra of the S-carboxymethyl derivatives of ovothiols C(top), B(middle), and A(bottom) at neutral pH; the insert detail is from 3–4 ppm. Spectra of $D_2O$ solutions were obtained with a spectral width of 5000 Hz (10 ppm), acquisition time of 1.6s, and a relaxation delay of 4s. The pD, uncorrected, was 6.5–7.5 for all spectra.

Comparison of the spectrum of derivatized ovothiol C with that of the underivatized molecule revealed that the carboxymethyl proton resonance appears at 3.3 ppm, overlapping with the downfield $C^\beta H$ resonance. Integration of the spectrum shown in FIG. 3 (top) confirms this assignment, as the complex group of peaks at approximately 3.3 ppm contains the intensity of three protons. The other resonance assignments for ovothiol C are identical to those already published: imidazole C-2 H, 7.52 ppm; $C^{60}H$, 3.59 ppm; $C^{\beta,\beta'}H$, 3.3 ppm, 3.06 ppm; N-1 $CH_3$, 3.53 ppm; $\alpha N-(CH_3)_2$, 2.77 ppm. The spectra of ovothiol A and ovothiol B are very similar to that of ovothiol C. The major differences in the spectra are in the upfield singlet peak. This appears as a six-proton resonance at 2.77 ppm in ovothiol C, as a three-proton resonance at 2.52 ppm in ovothiol B, and is absent in the ovothiol A spectrum. Thus, ovothiol C, B, and A represent di-methyl, monomethyl, and des-methyl forms of the molecule. Resonance assignments for the ovothiol A and B spectra could be made by comparison with the oviothiol C spectrum, although nuclear Overhauser experiments were also performed to confirm the assignments and to determine the position of the ring N-methyl group (described below). The assignments for ovothiol A are: imidazole C-2 H, 7.56 ppm; $C^{60}H$, 3.81 ppm; ring N—$CH_3$, 3.52 ppm; $C^\alpha H$, 3.5 ppm; S-$CH_2$, 3.31 ppm; $C^{\beta,\beta'}H$, 3.11 ppm; αN—$CH_3$, 2.52 ppm. Proposed structures (reduced form) of ovothiol A, B, and C based on these data are shown below.

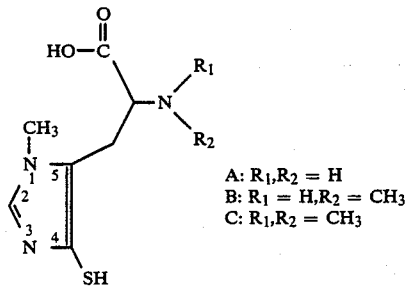

A: $R_1, R_2 = H$
B: $R_1 = H, R_2 = CH_3$
C: $R_1, R_2 = CH_3$

The coupling patterns observed for the S—$CH_2$ resonances in all three spectra and for the $C^\beta H$, $C^{\beta'}H$ resonances of ovothiol A and B are not those predicted by first order analysis (i.e., 2 doublet resonances for the carboxymethyl protons and two doublets-of-doublet peaks for the $C^\beta$ protons). The patterns observed occur under conditions were $(\nu_A - \nu_B)$ is the difference in chemical shift for the two coupled protons and J is the coupling constant between them.

Further confirmation of the structure of ovothiol A was obtained by removal of sulfur from the compound by the Raney nickel catalyst as previously reported for ovothiol C(Turner et al., 1986), followed by comparison of the 500 MHz NMR spectrum of the des-S-ovothiol A product which samples of authentic 1-methyl and 3-methylhistidine. Upon mixing with 3-methylhistidine, two peaks were clearly resolved for the N-methyl and two aromatic protons. When des-S-ovothiol A was mixed with 1-methylhistidine only single peaks were observed, indicating that the compounds were identical. Replacement of sulfur with hydrogen by Raney nickel also confirmed C-4 as the site of the sulfur atom in ovothiol A. In des-S-ovothiol A a new aromatic proton appeared at 6.75 ppm, upfield from the existing proton at 7.5 ppm; based on the chemical shifts of the aromatic protons of the parent compound imidazole, this is consistent only with an original proton located at C-2 and a sulfur at C-4.

Figure 4:
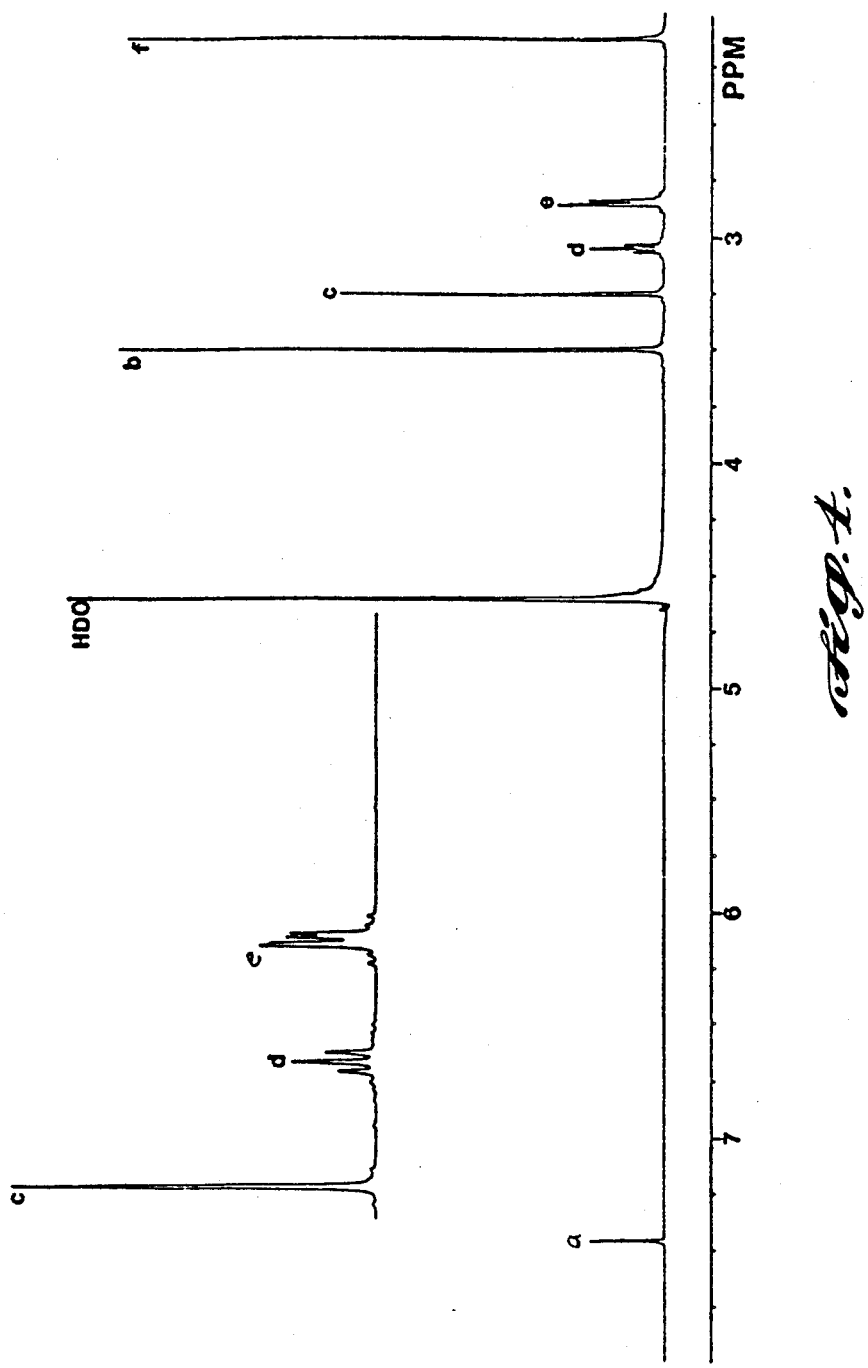
FIG. 4 presents data demonstrating a refinement of the 4-thiohistidine isolation protocol set forth in Example 1.

Because an authentic standard for des-S-ovothiol B was not available, Nuclear Overhauser Effect (NOE) studies were performed on S-carboxymethyl ovothiol B. Reference $^{1}H$-NMR spectra for NOE were taken at pD of approximately 12 (FIG. 4), which allowed resolution of the α-methine proton and N-1 methyl groups which overlapped in the neutral pD spectrum (FIG. 3, middle). NOE experiments were run as automatic difference spectra, with a cycle of 8 on-resonance and 8 off-resonance scans. In FIG. 4, insert detail is from 2.3–3.3 ppm; aquisition parameters are the same as in FIG. 3.

Referring to FIG. 4, peak a represents a single aromatic proton, b a methyl linked to aromatic nitrogen, c the methylene of the S-carboxymethyl group, d the $C^\alpha$ proton, e the β methylene group, and f the α-amino methyl group. In NOE studies, only peaks b and c were irradiated. Peak b gave an NOE to peaks a, d, and e; no NOE was seen from peak C. The position of the imidazole ring methyl group was thus confirmed as N-1 by the observed NOE from the ring methyl group (peak b) to the α-methine and β-methylene protons (peaks d, e). A methyl group at N-3 would not be expected to give these NOEs. The absence of NOE from the sulfur-linked methlene group resulting from S-carboxymethylation again confirmed that the ring methyl group is linked to N-1, not adjacent to sulfur at N-3(see below).

In summary, the method of isolation and detection of 4-thiohistidines reported above, using S-carboxymethylation and ion-pairing HPLC, represents a significant improvement over isolation of the native material by ion-exchange HPLC as previously described (Turner et al., 1986). Because the S-carboxymethyl derivatives of the 4-thiohistidines are not redox labile, the problem of separation of multiple oxidation states (dimer vs. monomer) does not complicate the isolation procedure. Quantities in the range of 0.1 ∝ 1.0 nmol are detectable by UV absorbance at 210 nm, and quantitation is facilitated by incorporation of a label of known specific activity.

EXAMPLE 2

A general synthetic entry to the ovothiols: synthesis of L-ovothiol A

A synthesis of L-ovothiol A(6), a thiolhistidine derivative of marine origin, is reported. The route features a new and mild synthesis of substituted thiol imidazole derivatives, from which structural and isotopically labeled analogs of the ovothiol family can be readily achieved.

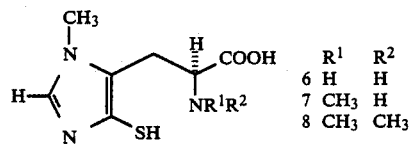

| | R¹ | R² |
|---|---|---|
| 6 | H | H |
| 7 | CH₃ | H |
| 8 | CH₃ | CH₃ |

The S-protected thiol imidazole 11 was prepared in two synthetic operations from 9 using a new synthesis of thiol imidazoles which was developed specifically for this purpose.

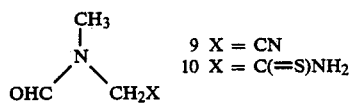

9 X = CN
10 X = C(=S)NH₂

An ethanolic solution of N-cyanomethyl-N-methylformamide 9 [prepared in 50% overall yield by cyanomethylation of methylamine ($CH_3NH_3^+Cl^-$, NaCN, $CH_2O$, $H_2O$, 0°→25° C.) followed by formylation ($HCO_2Ac$)] and triethylamine at 25° was treated with hydrogen sulfide (Rec. Trav. Chim. 51:72, 1931) until analysis (TLC on $SiO_2$) indicated complete conversion to the corresponding thionamide 10 which crystallized from the reaction mixture upon cooling (80%, m.p. 89°–91° C.). [Yields are reported for spectroscopically homogeneous materials whose structures were supported (unless otherwise specified) by ¹H NMR, IR, MS, and, where applicable, UV.] Conversion of thionoamide 10 to the protected heterocycle 11 was achieved by suspension of 10 in dichloromethane at 25° C. and sequential treatment with 6 equiv. of triethylamine and 4.5 equiv. of chlorotrimethylsilane. [Formic acid (reflux. 12 h) was also effective for this transformation. Alternatively, for a significantly milder method than either of the foregoing, trimethylsilyl trifluoromethanesulfonate (at 78° C., in most cases; see Spaltenstein, A., et al., J. Org. Chem. 52:2977–2979, 1987) may be used in place of chlorotrimethylsilane.] After 12 h the solution was concentrated in vacuo, redissolved in ethanol, cooled to 0° C. and treated sequentially with an excess of sodium borohydride and 1 equiv. of p-methoxybenzylchloride (0.5 h, 25° C.). Chromatography on silica gel afforded heterocycle 11 in 81% yield.

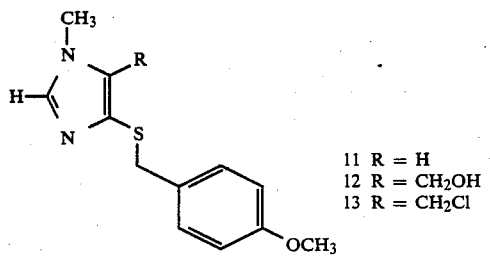

11 R = H
12 R = CH₂OH
13 R = CH₂Cl

Hydroxymethylation on C-5 of protected thiol imidazole 11 ($CH_2O$ in aqueous NaOAc/HOAc buffer, pH 4.6, reflux. 1.5 h) (Chem. Pharm. Bull. 22:2359, 1974) gave the crystalline trisubstituted imidazole 12, m.p. 113°–114° C. (EtOAc) (73%), which was converted to the hydrochloride salt of 13 ($SOCl_2$, 0.5 h, 25° C.).

The bis-lactim ether 14 (3 equiv.) derived from D-valine was metalated (n-butyl lithium (BuLi), tetrahydrofuran (THF), −78° C.) and treated with the hydrochloride salt of 8 (−78° to 25° C.) (Top. Curr. Chem. 109:66, 1983; Pure Appl. Chem. 55:1799, 1983) to yield 15 and its epimer at the newly formed chiral center in a 3.2:1 ratio (combined yield, 64%).

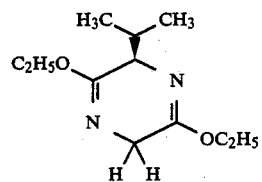

14

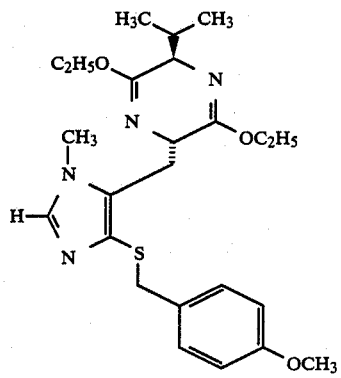

15

The epimers were separated on silica gel, the assignment of the major isomer as the trans-disubstituted bidlactim ether 15 being well precedented (Top. Curr. Chem 109:66, 1983; Pure Appl. Chem. 55:1799, 1983) and confirmed by successful conversion to the natural product. Hydrolysis of the fully functionalized protected thiolhistidine 15 (aqueous HCl, 25° C. to reflux) gave the thiol-protected amino acid 16 (58%), which was chromatographically separated from the coproduct, D-valine.

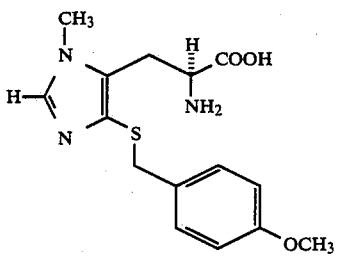

16

Figure 5:
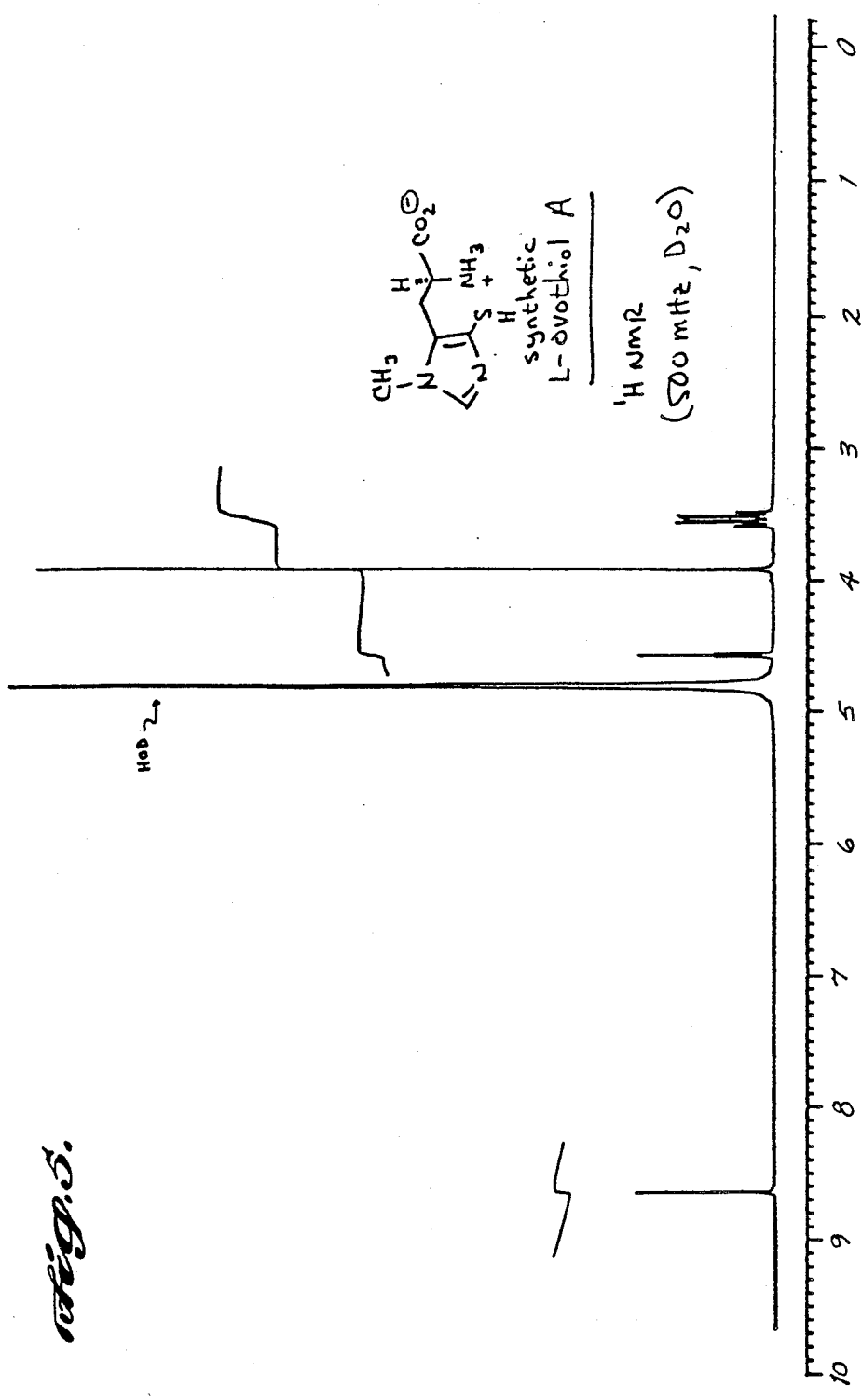
FIG. 5 presents data confirming the 4-thiohistidine synthesis protocol described in Example 2.

Finally, removal of the p-methoxybenzyl protecting group with mercuric trifluroacetate in trifluoroacetic acid/anisole (Chem. Phar. Bull. 26:1576, 1978; or with anhydrous HF and o-cresol at 25° C.) afforded ovothiol A (6, 94%), which was identical to a sample of naturally derived ovothiol A by both 500 MHz ¹H NMR (see FIG. 5) and UV.

Air oxidation of synthetic ovothiol A [in the presence of a trace of Cu(II)] followed by chromatography on Sephadex LH-20 (80% aqueous ethanol) afforded the disulfide form of ovothiol A, $[\alpha]_D^{20}+77°$ (c=6.5 mg/ml in 0.1M HCl), which was again identical to a sample of the natural disulfide by 500 MHz $^1$H NMR and UV. The observation of a single diastereoisomer of synthetic ovothiol A disulfide in the $^1$H NMR verifies the optical purity of the synthetic material (see below).

The availability of synthetic (+)-ovothiol A disulfide has aided the assignment of the absolute configuration of the ovothiol family. At the time this synthesis was completed, the absolute configuration of naturally derived ovothiol A was unknown, and furthermore, the natural material was sufficiently precious that the specific rotation had not been measured. In the course of the synthesis, it was noted that the two diastereomeric disulfides resulting from air oxidation of synthetic ovothiol A of low enantiomeric excess (available by virtue of the less than complete sterospecificity of the bis-lactim ether alkylation step) were readily distinguished by 500 MHz $^1$H NMR. Thus, the finding that a 1:1 mixture of synthetic ovothiol A(6, thiol form), and naturally derived ovothiol A (6, thiol form) provided on air oxidation a single disteroisomer of the disulfide (500 MHz $^1$H NMR analysis) clearly demonstrates the stereochemical identity of the synthetic and natural material. Since the synthetic disulfide is dextrorotatory, and it is now know (see Example 3) that the thiolhistidines previously isolated and assigned, in the disulfide form, to the L-(+)-series by other investigators are identical to the ovothiols, it follows that natural ovothiol A (6, from the Strait of Juan de Fuca) possesses the L-configuration. Furthermore, the specific rotation of natural ovothiol A has been measured and confirms the NMR-based arguments herein.

In summary, these studies confirm the formulation of ovothiol A as 6, a structure previously proposed (Turner et al., 1986) on the basis of spectroscopic data and chemical degradation. The synthesis has been readily modified to provide ovothiol C(8), as disclosed in Example 3, and provides a general route to afford synthetic ovothiol B (7) and ovothiol analogs, all of which are considered to be of interest for clinical studies. As an indication of its ready applicability, this new synthesis of thiol imidazoles under mild conditions using a silylating reagent has been used to prepare a variety of thiol imidazoles; see Example 4.

EXAMPLE 3

Synthesis and structure reassignment of thiolhistidines of marine origin

The structure of ovothiol C, a thiolhistidine derivative isolated from the eggs of sea urchin, has been confirmed by synthesis to be 17b and shown to be identical to a substance formerly incorrectly assigned the structure 18b.

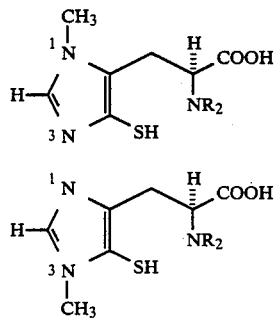

a R = H b R = CH$_3$

We recently reported the isolation and identification of 1,N$\alpha$,N$\alpha$-trimethyl-4-thiolhistidine (ovathiol C, 17b) from the eggs of S. purpuratus, a sea urchin indigenous to the west coast of North America and collected from the Strait of Juan de Fuca (J. Biol. Chem. 260:13163, 1985; J. Biol. Chem. 261:13056, 1986). More recently, we have isolated and identified the homolog 17a (ovothiol A) from other local marine sources.

Interestingly, Italian investigators had previously claimed to have isolated and identified the methylated thiolhistidine derivatives 18a and 18b, the 3-methyl isomers of 17a and 17b, respectively, from the eggs of closely related marine organisms collected in the bay of Naples. Ito, S., et al., J. C. S. Chem. Commun. 1042, 1976; Ito, S., et al., Experientia 35:14, 1979; Nardi, G., et al., Comp. Biochem Physiol. 71B:297, 1982; Polumbo, A., et al., Tetrahedron Lett. 23:2307, 1982; Palumbo, A., et al., Comp. Biochem Physiol. 78B:81, 1984; Rossi, F., et al., Comp. Biochem. Physiol. 80B:843, 1985.

We have found no evidence for the presence of 3-methyl-4-thiolhistidines in marine organisms collected in the Pacific Northwest; the Italian investigators make no mention of having observed 1-methyl-4-thiolhistidines. While it seemed probable that one team or the other had erred, the discordant assignments were reached through virtually identical experiments involving Raney nickel desulfurization of naturally derived materials followed by careful comparison to both 1- and 3-methyl-L-histidines (J. Biol. Chem. 261:13056, 1986; Comp. Biochem. Physiol. 7813:81, 1984). We have pursued this inconsistency, and report here that the structure 17b which we have assigned to ovothiol C has been confirmed by independent chemical synthesis. Additionally, we present evidence that the 3-methyl-4-thiol-L-histidines which have previously appeared in the literature should be reformulated as 1-methyl-4-thiol-L-histidines.

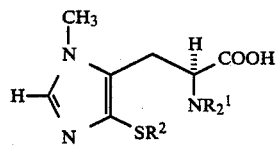

19 R$^1$ = H, R$^2$ = CH$_2$C$_6$H$_4$—p-OCH$_3$
20 R$^1$ = CH$_3$, R$^2$ = CH$_2$C$_6$H$_4$—p-OCH$_3$

Figure 6:
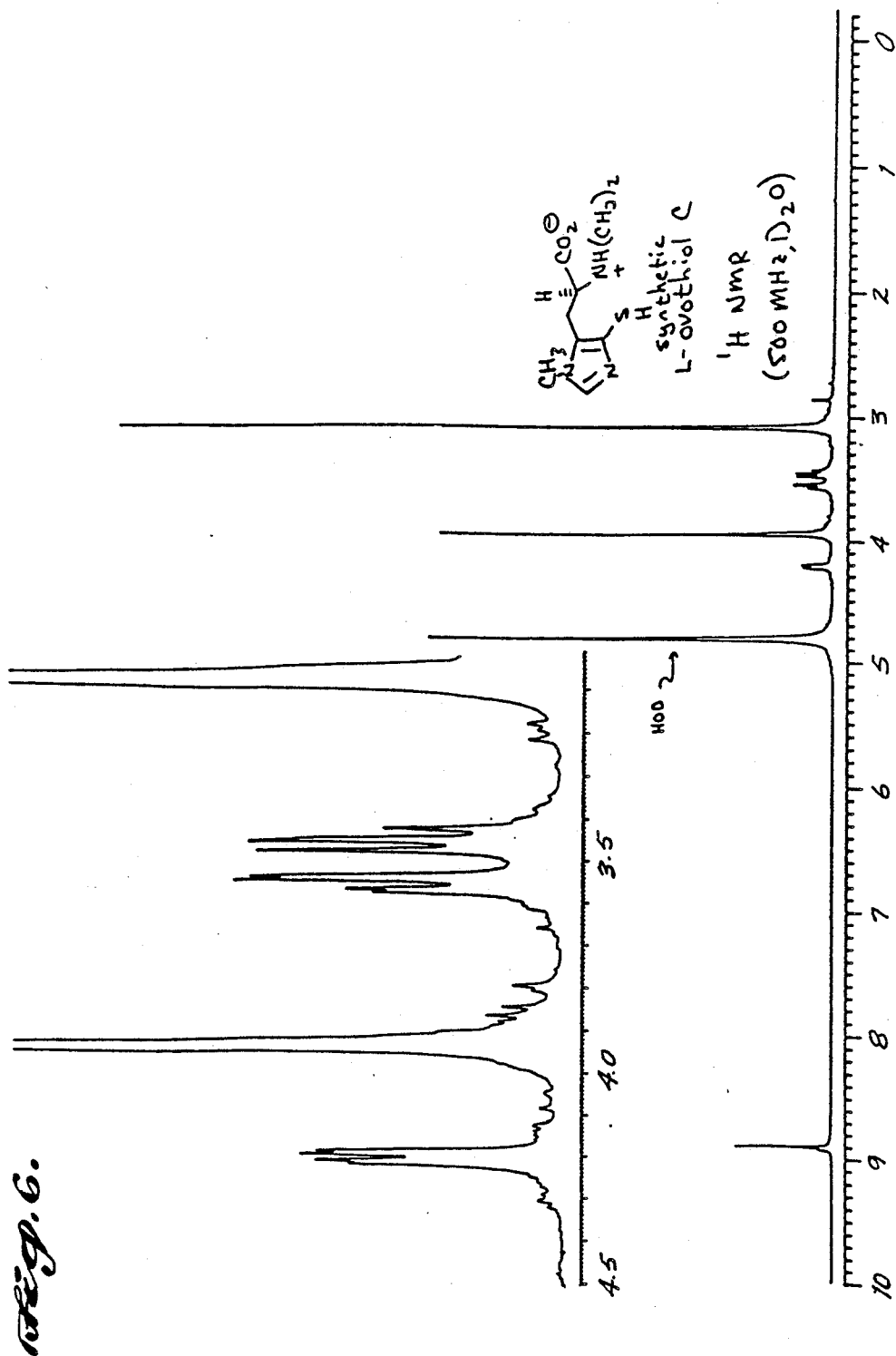
FIG. 6 presents data confirming the 4-thiohistidine synthesis protocol described in Example 3.

The penultimate product 19 in our synthesis of L-ovothiol A (17a), from Example 2, was diverted to L-ovothiol C (17b) by a two step process. Reductive methylation of 19 (CH$_2$O, H$_2$O, Pd/C, H$_2$) (J. Org. Chem. 11:258, 1968) afforded the $\alpha$-dimethylamino acid 20 (50%). Deprotection of the thiol group [Hg(O-COCF$_3$)$_2$/HOCOCF$_3$/anisole] (Chem. Pharm. Bull. 26:1576, 1978) afforded L-ovothiol C (17b, 86%), which was identical (500 MHz $^1$H NMR (see FIG. 6), UV) with a sample isolated from sea urchin eggs collected in the Strait of Juan de Fuca. Air oxidation of the synthetic thiol [trace Cu(II) required for complete conversion] afforded a disulfide, $[\alpha]_D^{20}+70°$ (c=10 mg/mL, H$_2$O), which was identical to the natural ovothiol C disulfide by the same criteria. Furthermore, these physical properties were essentially indistinguishable from those reported (Comp. Biochem. Physiol. 78B:81, 1984)

for the disulfide of the putative 3-methyl isomer, 18b. Fortunately, a sample of the substance previously identified as the disulfide of 18b became available to us. Careful inspection of the $^1$H NMR spectrum (500 MHx, D$_2$O) of the oxidized form of naturally derived samples of 17b and the putative 18b (and a mixture thereof) unequivocally supported the structural identity of the two samples.

Since the structure of 17b has been secured by synthesis, and the $^1$H NMR spectra of the disulfides of 17b and the putative 18b support their structural identity, it is now clear that the thiolhistidine derivatives isolated independently from marine organisms in the bay of Naples and the Strait of Juan de Fuca are identical, and that all of these substances belong to the 1-methyl-4-thiolhistidine family (i.e., 17). The incorrect assignments appear to have resulted from confusion regarding the nomenclature of histidine derivatives, having hinged on the observation by the Italian investigators that desulfurization of 18a provided "1-methylhistidine [distinguished from 3-methylhistidine] by comparison with authentic samples." This result is fully consistent with our own desulfurization experiment. Unfortunately, the nomenclature of ring-substituted histidines is ambiguous, and the illustrations in these papers indicate that the authors incorrectly formulated their authentic sample of 1-methylhistidine as its ring-substitution isomer. This led them to incorrectly formulate all members of the ovothiol family. Reinterpretation of the earlier experiments does not alter the prior assignment of these amino acids to the L-family. In conclusion, all of the 3-methyl-4-thiol-L-histidines formulated in the prior art should be reformulated as the isomeric 1-methyl-4-thiol-L-histidines.

EXAMPLE 4

Synthesis of 4-imidazolethiol ovothiol analogues

The ovothiol analogue H3 (1,5-dimethyl-4-mercaptoimidazole), in which the amino acid side chain of histidine has been replaced by a methyl group, and related 4-imidazoles were synthesized as described below. H3 and related 4-thioimidazoles have distinctive redox characteristics similar to the 4-thiohistidines, and are likely to be membrane permeant.

Figure 7A:
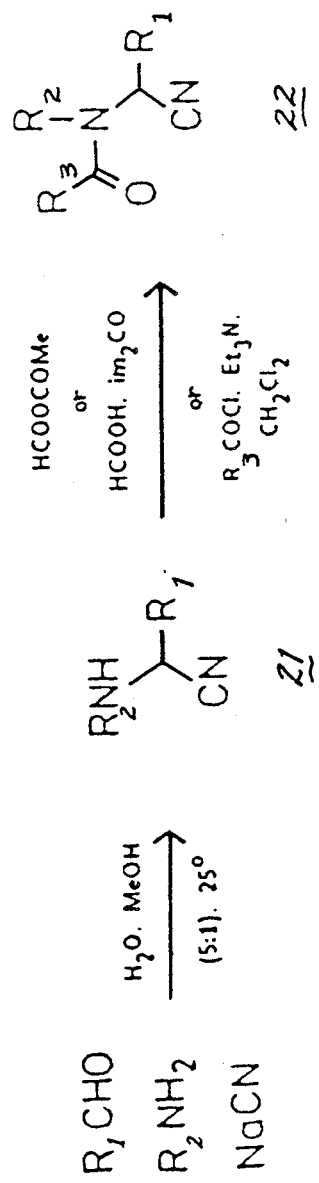
FIGS. 7A, 7B and 7C present an overview of the 4-thioimidazole synthesis protocol described in Example 4.
Figure 7B:
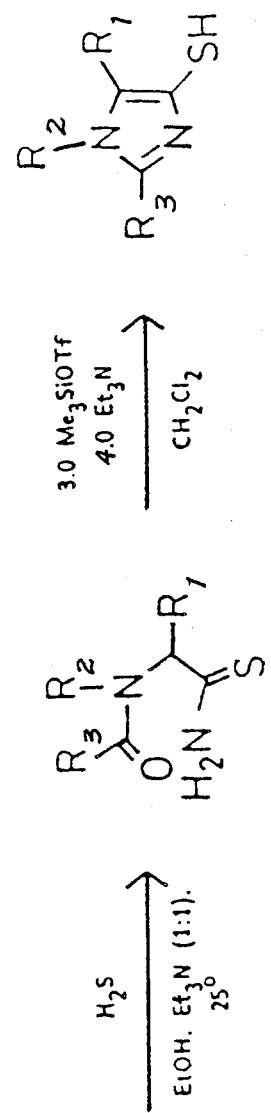
Figure 7C:
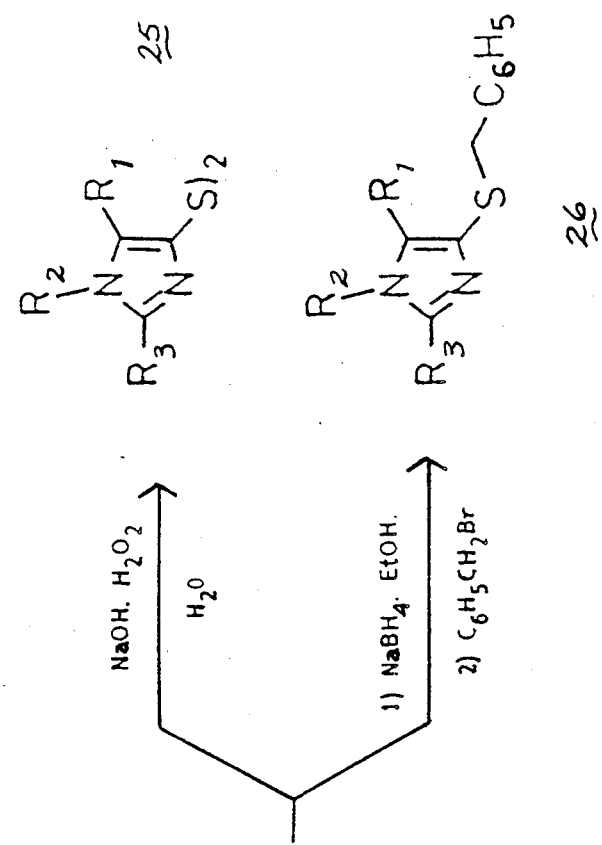

FIG. 7 summarizes the preferred 4-imidazolethiol synthesis, which is described in detail in Spaltenstein, A., et al., J. Org. Chem. 52:2977-2979, 1987, hereby incorporated by reference. Conversion, under standard conditions, of an aldehyde and primary amine to the corresponding cyano amine 21 followed by acylation gave the nitrile amide 22. Addition of hydrogen sulfide to the nitrile took place under mild conditions to afford cyclization substrate 23. Cyclization of 23 was accomplished with trimethylsily triflate and triethylamine in methylene chloride to yield 24. The imidazolethiol 24 may be isolated by a hydrolytic and extractive workup, followed by chromatography of the crude product on silica gel, but purification of the product is, in general, facilitated by masking of the thiol function. Thus, the disulfides 25 and sulfides 26 were more commonly isolated. Specifically, oxidation of 24 to the disulfide 25 or alkylation of 24 to the sulfide 26 were as shown.

Table 2 illustrates the structures of exemplary substituted 4-imidazolethiols that have been prepared by this method.

TABLE 2

| | Synthesis of 4-Imidazolethiols | |
|---|---|---|
| $R_2$ | $R_3$ | $R_1$ |
| 1 | CH$_3$ | H | H |
| 2 | n-C$_4$H$_9$ | i-C$_3$H$_7$ | i-C$_3$H$_7$ |
| 3 | n-C$_4$H$_9$ | C$_6$H$_5$ | i-C$_3$H$_7$ |
| 4 | CH$_3$ | H | CH$_2$OTHP |
| 5 | CH$_3$ | H | CH$_2$OCH$_2$C$_6$H$_5$ |
| 6 | CH$_3$ | H | CH$_2$CH$_2$OCH$_2$C$_6$H$_5$ |
| 7 | CH$_3$ | H | CH$_2$CH=C(CH$_3$)$_2$ |

EXAMPLE 5

Screening I: Reaction of aromatic thiols with oxygen radicals

Upon isolation or synthesis, the ovothiols and ovothiol analogues can be screened for redox activity as follows. Although aliphatic thiols have been extensively investigated (e.g., Jocelyn, P. C., Biochemistry of the SH Group, Academic Press, N.Y. 1972), the reactivity of aromatic thiols with partially reduced oxygen species has been less well studied (Munday, R., J. App. Toxicol. 5:402, 1985; Munday, R., J. Appl. Toxicol. 5:409, 1985; Munday, R., and E. Manns, J. App. Toxicol. 5:414, 1985), presumably due to the toxicity of the archetype, thiophenol. The apparent lack of toxicity of the ovothiol compounds is therefore encouraging, especially since aromatic thiols are more reactive toward oxidants other than their aliphatic counterparts. Described below are representative protocols by which the redox activity of aromatic thiols of this type can be readily assayed.

Direct reaction with H$_2$O$_2$

Our preliminary results indicated that the second order rate constant for ovothiol reacting with H$_2$O$_2$ was 3.34M$^{-1}$S$^{-1}$, some 2.3-fold greater than the rate with reduced glutathione. These preliminary studies were done in metal-free solutions containing EDTA, so additional experiments can compare the effect of ions of Fe, Mn, and Cu, as well as certain liganded derivatives such as hematin and vitamin B$_{12}$, on the reaction. We anticipate a more rapid rate, since aliphatic thiols react with H$_2$O$_2$ in a metal catalyzed reaction that is faster than in the presence of chelators (Pascal, I., and D. S. Tarbell, J. Am. Chem. Soc. 79:6015-6018, 1957; Schoberl, A., Hoppe Seyles Z. fur Phys. Chem. 201:107-109, 1931). Oxidation of ovothiol can be monitored by its absorbance change at 310 nm (Turner et al., 1986) and glutathione by coupling the reaction to glutathione reductase and NADPH oxidation.

Direct reaction with O$_2^-$·

The ability of ovothiol-like compounds to act as a superoxide dismutase (SOD) can be tested by assaying the disappearance of O$_2$·$^-$ from an aqueous solution of KO$_2$ at alkaline pH (Marklund, S. L., J. Biol. Chem. 251:7504-7508, 1976). Other thiols and redox-active metals can likewise be examined in this assay.

Xanthine oxidase-dependent oxyradical production

Xanthine oxidase with both acetaldehyde and xanthine as substrates (both xanthine and its product uric acid react with OH·) are used to determine whether the aromatic thiols or glutathione are oxidized by this reaction, or whether they inhibit cytochrome C reduction (McCord, J. M., and I. Fridovich, J. Biol. Chem.

244:6049-6054, 1969; Crapo, J. D., et al, Methods in Enzymology 530:382-386, 1977). For example, the ovothiol analogue H3 is oxidized by the xanthine/xanthine oxidase system, and that this can be suppressed by up to 50% by addition of SOD. Since GSH is protected only 20% by SOD in this assay (Wefers, H., and H. Sies, Europ. J. Biochem. 137:2936, 1983; Ross, D., et al., Biochem. Biophys. Acta 841:278, 1983), this implies a higher reactivity of 4-mercaptohistidines toward $O_2 \cdot^-$. Differences between the reactions with acetaldehyde and xanthine will implicate $OH \cdot$ in the process.

Inhibition of pyrogallol autooxidation

The inhibition of the air oxidation of pyrogallol has been used previously as an assay for superoxide dismutase (SOD) (Marklund, S., and G. Marklund, Eur. J. Biochem. 47:469, 1974; Roth, E. F. Jr., and H. S. Gilbert, Anal. Biochem. 137:50, 1984). The ovothiol analog H3 induces a time lag before initiation of the pyrogallol reaction. This lag is linearly dependent on the H3-concentration and is similar, though not identical, to the effect of thiophenol. In contrast, GSH had a more modest inhibitory effect and only at 50-fold higher concentration. The results suggest that ovothiol inhibits initiation or propagation of these oxidations by scavenging some intermediate. These reactions provide a simple system for discriminating between the properties of aliphatic and aromatic thiols.

Trapping of tyrosyl radicals

The known photochemical crosslinking of tyrosine (Amado, R., et al., Methods Enzymol. 107:377, 1984; Malencik, D. A., and S. R. Anderson, Biochem. 26:695, 1987; Joschek, H.-I., and S. I. Miller, J. Am. Chem. Soc. 88:3273, 1986) may be used as an assay for tyrosyl radical scavenging ability. This reaction proceeds by photochemical excitation of tyrosine, followed by an ejection of an electron to yield a tyrosyl radical. The ejected electron is apparently scavenged by oxygen, as evidenced by the augmentation of the tyrosine crosslinking rate on addition of SOD (scavenging $O_2 \cdot^-$, thus slowing the back reaction of tyrosyl radical and $O_2 \cdot^-$ to yield tyrosine and $O_2$). The tyrosyl radicals couple with one another to yield dityrosine, which is detected by its characteristic fluorescence. The ovothiol analog H3 is a strong inhibitor of photochemical dityrosine formation, slowing the reaction for several minutes at 1 $\mu M$ and effectively stopping it entirely for 5 to 10 min at 10 $\mu M$. Ascorbate and thiophenol at similar concentrations cause a similar inhibition; GSH is at least an order of magnitude less effective. This is strong evidence that ovothiol can act as an efficient tyrosyl radical scavenger. This assay is mechanistically relatively simple technique for assaying antioxidants.

Reaction with Fremy's salt

Fremy's salt $(K^+ {}^-O_3SN(O\cdot)SO_3^-K^+)$ is a stable, commercially available nitroxide radical. Reduction of this radical can be followed by UV or ESR. In comparison of the rates of reduction of Fremy's salt by the ovothiol analog H3, thiophenol, and glutathione, at pH 7.0, H3 is the fastest radical scavenger. It is roughly ten-fold faster than thiophenol and 40-fold faster than glutathione. In this assay, a relatively large difference was seen between two aromatic thiols, H3 and thiophenol.

Effect of aromatic thiols on salicylate oxidation in the fenton reaction

A mixture of $FeCl_2$ and $H_2O_2$, which by Fenton chemistry (reaction [2]) can produce $OH \cdot$, leads to formation of a colored product with salicylates. This reaction is stimulated greatly by thiols, e.g., glutathione has a maximum stimulation at around 70 $\mu M$ and inhibits at higher concentrations (Rowley, D. A., and B. Halliwell, FEBS Lett. 138:33-36, 1982, FEBS Lett. 142:39-41, 1982). The reaction is thought to involve $OH \cdot$ as an intermediate. As above, the subject aromatic thiols can be compared with glutathione as effectors of the reaction.

Reaction with $O_2$

The most chemically reasonable mechanism for the ovothiols' apparent ability to scavenge the $O_2 \cdot^-$, $H_2O_2$, and tyrosyl radicals is by acting as a reducing agent. Our preliminary results would therefore implicate ovothiol as a kinetically better reducing agent than glutathione. It is tempting to speculate that even better reducing agents might exist and surpass the ovothiols in ability to scavenge active oxygen. At some point, however, a sufficiently strong reducing agent will become able to reduce $O_2$ to $O_2 \cdot^-$ at a significant rate, playing the role of reactive oxygen generator in addition to scavenger. As a measure of ability to active $O_2$, the rates of air oxidation of GSH, ovothiol, and other aromatic thiols are compared in the absence and presence of metals. This assay might be generally useful in pinpointing active oxygen scavengers of inappropriately high reactivity.

The above protocols may be used to test whether 4-mercaptohistidines and the other subject thiols interact with $O_2 \cdot^-$ or $H_2O_2$ predominantly; they should also indicate whether reactivity occurs with $OH \cdot$. If, as contemplated, thiolhistidines play a physiological role in protecting from reactive oxygen, it would be at the level of $O^{2-} \cdot$, $H_2O_2$, or some other relatively long-lived reactive species rather than hydroxyl radical, which interacts with proximate cellular components soon after its generation.

EXAMPLE 6

Screening II: Protection of macromolecules from oxidative damage

Once isolated or synthesized and screened for redox activity, the subject aromatic thiols may be screened for ability to protect macromolecules from oxidative damage, as described below.

The molecular targets for oxidative stress include membranes, protein, and nucleic acid. The protectant effect of 4-mercaptohistidines (and other aromatic thiols) on such reactive oxygen mediated damage can be assessed by available techniques. This screening step would be of interest, since the actual intermediate in causing damage in the macromolecular systems may be different from one of the oxygen radicals that initiate the process. For example, peroxyl, alkoxyl, tyrosyl, and other free radicals have been implicated in pathogenesis of disease (e.g., Mason, R. P., and C. F. Chignell, Pharmacol. Rev. 33:189-211, 1982; Free Radicals in Molecular Biology, Aging, and Disease, Aging 27 (entire volume), 1984; Free Radicals and Cancer, ed. R. Floyd, Marcel Dekker, NY, 1982). Mercaptohistidines might block the production of such radicals or terminate their chain reactions. Several in vitro modifications of the major classes of macromolecules can be characterized to interpret the later results on intact cells (Example 7). In every case aliphatic thiols are compared with aromatic thiols, especially looking for specific effects of the 4-mercaptohistidine and other derivatives and analogues.

A. Lipid Peroxides

Lipid peroxide damage, generated by a radical reaction, has been implicated in cellular oxidative stress. Reactive oxygen intermediates are one source of initiation of these reactions. The subsequent formation of lipid radicals that react with molecular oxygen to produce peroxyl radical chain reactions (Porter, N. A. Methods in Enzymol. 105:273–282, 1984; Kappus, H., in Oxidative Stress, ed. H. Sies, pp. 273–310, Academic Press, N.Y., 1985; Aust, S. D., J. Free Rad. Biol. Med. 1:3–25, 1985) propogates the damage; redox active metal ions also play a role. A frequent assay for lipid peroxidation involves measurement of thiobarbituric acid (TBA)-reactive substances, which include malondialdehyde. Ovothiols and aliphatic thiols are thereby compared for their ability to inhibit damage to lipids.

B. Protein Damage

Although oxidatively modified proteins are rapidly degraded by selective intracellular proteolysis, the mechanisms by which these proteins are recognized and the types of modifications introduced are only beginning to be characterized. Whereas the individual reactive oxygen species responsible for critical damage are not certain, recent work strongly implicates OH· as the responsible agent (Davies, K. L., J. Biol. Chem. 262:9895–9901, 1987), with $O_2^-$ alone having little effect. A mixture of $O_2^-$ and OH· leads to direct protein modification and fragmentation (Davies, K. J. A., et al., J. Biol. Chem. 262:9902–9907, 1987; Davies, K. J. A., and M. E. Delsignore, J. Biol. Chem. 262:9908–9913, 1987; Davies, K. J. A., J Biol. Chem. 262:9914–9920, 1987). We use bovine serum albumin (BSA) as a model protein and generate reactive oxygen species either with acetaldehyde and xanthine oxidase, xanthine and xanthine oxidase, $H_2O_2$, or ascorbic acid and iron, systems described above that have previously been used to monitor amino acid modifications (Davies, K. J. A., and A. L. Goldberg, J. Biol. Chem. 262:8220–8226 and 262:8227–8234, 1987). We look for loss of tryptophan fluorescence and dityrosine production, both of which indicate free radical damage to proteins. Protein covalent crosslinking to form dimers, trimers, and tetramers accompanies dityrosine formation, and this can be examined by SDS-polyacrylamide gel electrophoresis. These assays indicate whether one obtains the expected classes of amino acid modification previously seen with $^{60}Co$ irradiation of BSA. Catalase and SOD can be employed to examine the specificity of the changes for $H_2O_2$ and $O_2^-$, respectively, as well as putative OH· scavengers such as mannitol. Since the oxidative changes leading to proteolysis were only marginally affected by dithiothreitol, this allows a comparison of the relative efficacy of 4-mercaptohistidines and other thiols vs. "classical" oxygen radical scavengers in a well-characterized model system.

C. Nucleic Acid Damage

Mutation and chromosome breakage are two lesions of DNA that have been postulated to explain the cellular pathology of carcinogenesis. The effects of 4-mercaptohistidines and related compounds are evaluated, on a well-characterized system for inducing lesions with Fe, that is radiomimetic in that it leads to single strand breakage that can be readily assessed by relaxation of supercoiled DNA (Repine, J. E., et al., Proc. Nat. Acad. Sci. USA 78:1001–1003, 1981; Schulte-Frohlinde, D., and C. Von Sountag, in Oxidative Stress, ed. H. Sies, pp. 11–40, Academic Press, N.Y., 1985).

EXAMPLE 7

Screening III: Inhibition of the cellular damage caused by oxidative stress

The next screening is for whether the subject thiols protect cells from oxidative stress. Many systems have been tested for oxidative damage, among which the following provide an opportunity to ask specific questions with regard to particular mechanisms of oxygen toxicity.

This aspect of the screening program introduces additional complications. For example, certain thiols are toxic to cells (Heinecke, J. W., et al., J. Biol. Chem. 262, 1987; Issels, R., et al., in Superoxide and Superoxide Dismutase in Chemistry, Biology, and Medicine, ed. G. Rotilio, pp. 419–421, Elsevier, N.Y., 1986) because they can autooxidize and produce reactive oxygen intermediates (Misra, H. R., J. Biol. Chem. 249:2151–2155, 1974). Thiol toxicity may be due to redox cycling; for example, when cystine is given to cells it damages lipoproteins, apparently by being reduced to cysteine intracellularly then exiting to reoxidize and produce oxygen radicals and cellular damage. When we administered compound H3 (containing the reactive 4-mercaptoimidazole ring without the amino acid side chain) to sea urchin eggs, it was toxic at 2 mM but not at 200 μM (as assessed inhibition of the first cellular division after fertilization). When H3 was given to cultured myoblasts, it inhibited colony formation at 200 μM with a half-maximal effect on $^3$H-TdR incorporation at 15 μM. We tried compound H3 because we thought it would be permeant, having no charged side chain; we administered it to these cells as the disulfide. We infer that the toxicity was caused by redox cycling, with H3 being taken up, reduced, and the thiol being reoxidized extracellularly to produce reactive oxygen intermediates. Although this compound may be protective from oxidative stress at lower concentrations, at these concentrations it clearly has the capacity to be toxic, a point that should be kept in mind in screening derivative compounds according to the protocols below. The amino acids, such as ovothiol A and C, are less likely to engage in redox cycling once they enter cells, for they do not exit from eggs (Turner, E., et al., Biochem. 26:4028–4036, 1987, hereby incorporated by reference).

First, the conditions under which ovothiols A or C are transported into the cells of interest are determined using radioactive ovothiol derivatives. For example, by reacting ovothiol A with $^3$H-formaldehyde and reduction by NaBH$_4$, ovothiol A was converted into $^3$H-ovothiol C. Preliminary results indicate that fertilized sea urchin eggs incubated with $^3$H-ovothiol C accumulate the amino acid at 6 fmol/egg/hr, as compared with histidine uptake of 38 fmol/egg/hr. The $k_m$ for OSH uptake appears to be higher than for histidines, although the $V_{max}$ may be similar. We measure the kinetics of ovothiol uptake into the cells to be studied, in order to identify optimal conditions for transport. We no only use $^3$H-ovothiol C but also synthesize $^3$H-ovothiol A by using $^{14}C$—HCHO in the abovedescribed chemical synthesis procedure. We do not know why ovothiol exists in $N^\alpha$-methylated and unmethylated forms in different species, but one possibility is that the methyl groups affect transport of the amino acid across the plasma membrane to ensure that it remains intracellular.

Ovothiols may enter cells via the histidine transport mechanism, but H3 (lacking the amino acid side chain) probably enters by diffusion with cellular toxicity due to redox cycling as discussed above. We think the ovothiols will not engage in redox cycling since they clearly are not toxic to eggs, although they are transported into them. One can readily assess whether ovothiols are less toxic than H3 in the endothelial and other cells to be studied. Any utility of the ovothiols as physiological protectants will depend upon their being accumulated by cells and not undergoing significant redox cycling. Thus these transport and cellular toxicity experiments are prerequisite to analyses of cellular protection from oxidative stress and cellular toxicity. The general protocol is to try ovothiol, its congeners, ergothioneine, and other thiols as protectants or facilitators of damage in certain complementary cell systems.

Red blood cell damage by oxygen radicals

Mammalian erythrocytes, as anucleate cells with defined lifespan, afford an attractive model system for exploring the cell biology of reactive oxygen. They contain large quantities of the iron protein, hemoglogin, which produces reduced oxygen intermediates continuously due to autooxidation (Misra, H. P., and I. Fridovich, J. Biol, Chem. 247:6960–6962, 1972, Stern, A., in Oxidative Stress, ed. H. Sies, pp. 331–345, Academic Press, N.Y., 1985; Weiss, S. J., et al., Proc. Natl. Acad. Sci. U.S.A. 77:584–587, 1986) in a process that is stimulated by many chemicals (Maridonneau, I., et al., J. Biol. Chem. 258:3107–3113, 1982; Cohen, G., and P. Hochstein, Biochem. 3:895–900, 1964). Oxygen radicals are implicated in the pathogenesis of sickle cell and unstable hemoglobin diseases, drug induced hemolysis, and other disorders (Hebbel, R. P., et al., J. Clin. Invest. 70:1253–1259, 1982; Flynn, T. P., et al., J. Clin. Invest. 71:1215–1223, 1983). The xanthine/xanthine oxidase, or $H_2O_2$ or $Fe^{2+}$/ascorbate systems (described above) both lead to protein degradation and lipid peroxidation in red blood cells, and the two degradative events appear to occur by distinct mechanisms. Protein degradation can be induced in the absence of lipid peroxidation and is not sensitive to antioxidants that block lipid damage. This system is excellent for assaying differential antioxidant behavior of OSH compared to other protectants, using, e.g., the rabbit erthrocyte model developed by Davies and Goldberg.

Bacterial mutants to evaluate antioxidant properties of ovothiols.

The rapid growth of bacteria and availability of specific mutants allow one to test some critical question about ovothiols and cellular protection. The following systems are exemplary.

Superoxide dismutase (SOD) deficient mutants

E. coli double mutants completely lacking SOD (i.e., deficient in both the Mn and Fe dependent enzymes) have highly enhanced mutation rates aerobic growth (Farr, S. B., et al., Proc. Nat. Acad. Sci. U.S.A. 83:8268–8272, 1986). Assays for growth and mutation (Touati, D., and A. Carlioz, in Physiology of Oxygen Radicals, eds. E. A. Taylor, et al., pp. 287–292, Am. Physiol. Soc., Bethesda, MD, 1986; Carlioz, A., and D. Touati, EMBO J. 5:623–630, 1986) in the presence of the subject thiols indicate their cellular protection efficiency, since the presence of either SOD of E. coli affords a high level of protection from reactive oxygen. This is a sensitive system for analyzing the cellular effects of aromatic thiols and should indicate whether ovothiol congeners can replace SOD physiologically.

Oxygen radical-sensitive Salmonella tester strains

A rapid screening procedure exists for identification of mutagens that are potential carcinogens (Ames, B. N., Science 221:1256–1264, 1983). One class of Salmonella mutant tester strains can be used to detect oxidative damage from bleomycin, $H_2O_2$, other hydroperoxides, streptonigrin, phenylhydrazine and X-rays (Levin, D. F., et al., Proc. Nat. Acad. Sci. U.S.A. 79:7445–7449, 1982; Proc. Nat. Acad Sci. U.S.A. 81:1686–1700, 1984; Ames, B. N., et al. Mutat. Res. 31:347–364, 1975). These strains, TA102 and TA104, which differ in the placement of the relevant his mutation (on plasmid or chromosome, respectively), have been used to examine the mutagenicity of many compounds thought to work via oxygen radicals. We explore whether ovothiol and other aromatic thiols influence the mutation rate induced by bleomycin, $H_2O_2$, phenylhydrazine and menadione. These data indicate whether the aromatic thiols can protect growing cells from mutation by oxidative damage to DNA in vivo. *Paraquat toxicity.* Paraquat is a quinone that undergoes redox cycling to lead to the production of $O_2^-$ and cellular damage, including mutation. Because this system for redox cycling has been well studied, it allows one to assess the potential role of thiols in blocking the redox cycling pathology induced by paraquat. It also provides an excellent model system for analyzing whether the non-amino acid 4-mercaptoimidazole H3 or ovothiols such as A and C engage in significant redox cycling. Thus, 4-mercaptohistidines and other thiols can be assayed for effect on the repair system induced by paraquat (J. Biol. Chem. 260:922–925, 1985; Arch. Biochem. Biophys. 206:414–419, 1981).

Endothelial cells and oxidative stress.

Mammalian endothelial cells are known to be highly sensitive to reactive oxygen damage cell and are targets for lethal damage in many disease states where oxidative damage is implicated, including stroke, myocardial ischemia, atherosclerosis, and respiratory distress syndrome. Mammalian cells utilize gluthathione peroxidase and catalase as detoxicants of $H_2O_2$; the activity of the former system can be modulated by changes in glutathione level (Ann. Rev. Biochem. 52:711–760, 1983; Science 220:472–477, 1983). We use the endothelial cell model system developed by Harlan et al. (J. Clin. Invest. 73:706–713, 1984) to explore the significance of the gluthathione redox cycle in protection from oxidative damage. This involves manipulations of gluthathione levels with buthionine sufloximine or reaction with diethylmaleate, both of which potentiate damage by extracellular oxidants generated by glucose/glucose oxidase. Endothelial cells are also sensitive to hyperoxia in culture and thus may provide a good model system for the study of protection from intracellularly generated oxidants.

Radioprotection

It has been known for over 50 years that oxygen potentiates the cellular damage induced by radioactivity. Moreover, thiols constitute the best class of radioprotectants, although many effective aliphatic thiols are toxic (Sulfur Containing Radioprotective Agents, in Int. Encyc. Pharm. and Therap. 79, Pergamon, N.Y.). We assess whether ovothiol and congeners protect from radiation damage.

For example, these compounds can be assessed in the RIF-1 tumor line with $^{137}Cs$ irradiation and measurement of survival curves as previously described (Radiation Res. 93:157–174, 1983). This readily studied, reproducible system allow us to assess whether cellular viability is enhanced by ovothiols at different levels of radiation exposure and how this correlates with the other properties of these aromatic thiols.

EXAMPLE 8

A putative mammalian analog of ovothiol

We have begun a series of experiments to search for ovothiol-like compounds in mammals. Glutathione peroxidases occur in mammals and birds, but have not been reported in many lower organisms (Method. Enzymol. 107:576–581, 1984); thus the possibility arises that ovothiols may be restricted to those organisms where glutathione peroxidase doe not exist. To look for ovothiol-like compounds in mammals, we have taken rabbit liver and used our iodoacetate derivatization procedure (see above) to label thiols. In the ion pairing HPLC system for the separation of ovothiols, the S-carboxymethyl derivative of the low-molecular weight material isolated from mammalian liver according to the ovothiol purification comigrated with ovothiol C. In this system, gluthathione migrated significantly ahead of ovothiol C, and ergothioneine far ahead of glutathione. On ion-exchange HPLC, the mammalian derivative gave overlapping, but distinct, peaks with the ovothiol C derivative. These data were encouraging in suggesting that an ovothiol might exist in mammalian cells, although it was present at only 2–10 μM, making analysis difficult. Enough of the carboxymethyl derivative was isolated to analyze by high resolution NMR, in an attempt to define the number and types of protons on the molecule. The mammalian compound that comigrated with carboxymethyl ovothiol C was not identical to ovothiol C; rather, it had an identical proton composition to the S-carboxymethyl ergothioneine derivative (i.e., no imidazole methyl group and 3 methyl groups on $N^\alpha$). The proton peak positions were distinct from ergothioneine, even when the two compounds were mixed in the same tube. The NMR spectrum was likewise distinct from ovothiol C, which is a positional isomer of ergothioneine, with a methyl group on the 1-position of the imidazole ring. Thus the mammalian compound is neither ovothiol nor ergothioneine by chromatographic and spectroscopic properties; we did not have enough for nuclear Overhauser assignment of the proton relationships. The critical point is whether the mammalian compound is a 4-mercapto-histidine, with the redox activity of ovothiol, or a relatively redox inactive 2-mercaptohistidine like ergothioneine.

To purify the mammalian compound and analyze its structure, rather than purify the S-carboxymethyl derivative, one should start with very large quantities of liver and isolate the compound in its unmodified state. This would allow one to test its redox properties as well as gathering enough for structural analyses. One can analyze its properties as described above for ovothiol. The purification of the S-carboxymethyl derivative of ovothiol is similar to that of the underivatized ovothiol, at least in the early stages. Consequently, one can use this purification protocol to obtain the mammalian compound for the functional assay in the ovoperoxidase-oxidase system or in the other systems described above. One can verify whether this mammalian compound is of interest when sufficient quantities of the redox active compounds are obtained for analysis. One can also derivatize other mammalian tissues with $^3H$-iodoacetate in order to see whether higher concentrations of a compound with the chromatographic properties of the S-carboxymethyl mammalian liver compound (i.e., like S-CM ovothiol C) are present in higher concentrations in tissues such as ovary or brain. Our studies to date have used rabbit organs; when one finds an optimal tissue source after the preliminary screen, one can consider using the bovine system, which should provide sufficient quantities of fresh material from meat-packing plants to initiate the purification. A particularly interesting cell source, although not likely to be quantitatively useful in the purification, is the neutrophil, since these mammalian cells are known to exploit the respiratory burst and may have defense systems similar to that of the sea urchin egg. When and if one becomes certain that this mammalian analog is not an uninteresting modification of ergothioneine but rather a redox active aromatic thiol, one can look for it in neutrophils and mammalian oocytes, for the disclosed radiochemical assay is sufficiently sensitive to detect the compound in small numbers of cells once one is certain of the chromatographic identification of authentic mammalian standards.

APPENDIX

Nomenclature of Substituted Mercaptohistidines

Two systems of nomenclature for the imidazole ring of substituted histidines have been used historically (IUPAC Commission on the Nomenclature of Organic Chemistry and IUPAC-IUB Commission on Biochemical Nomenclature, Biochemistry 14:449–462, 1975), with biochemists generally designating the side chain as C-5 and the adjacent nitrogen as N-1 and organic chemists designating the side chain as C-4 and the adjacent nitrogen as N-3. A third system has been suggested by IUPAC (1975) in which the nitrogen proximal to the side chain is designated $\pi$ and that distal to the side chain $\tau$, with organic chemistry notation for the other positions (i.e., side chain at C-4), but this system has not been widely used.

We have chosen to use consistently the system designating the $\pi$-nitrogen as N-1 and side chain as C-5 because of the longstanding biochemical usage of this convention. The formulas set forth in the foregoing specification and appended claims are understood to encompass other ionized states as well as tautomers of the subject molecules.

Registry No. GSH, 70-18-8; NAD(P)H-O$_2$ oxidoreductase, 9032-22-8; ovothiol B, 108418-14-0; ovothiol A, 108418-13-9; ovothiol C, 105496-34-2; iodoacetic acid, 64-69-7; S-(carboxymethyl)ovothiol A, 108418-15-1; S-(carboxymethyl)ovothiol B, 108418-16-2; S-(carboxymethyl)ovothiol C, 108418-17-3; ovothiol A disulfide, 73491-33-5; des-S-ovothiol A, 368-16-1; ovoperoxidase, 9003-99-0.

All of the publications that are cited in the foregoing specification are hereby incorporated by reference.

While the present invention has been described in conjunction with preferred embodiments and specific examples, one of ordinary skill after reading the foregoing specification will be able to effect various changes, substitutions of equivalents, and other alternations to the compositions and methods set forth herein. For example, chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative convention reagents, by routine modification of reaction conditions, etc., or other reactions disclosed herein or otherwise conventional will be applicable to the preparation of the corresponding compounds of this invention. Similarly, the foregoing screening and therapeutic administration protocols are merely exemplary, and not limitative of the remainder of the disclosure in any way whatsoever. It is therefore intended that the protection granted by Letters Patent hereon be limited only to the definition contained in the appended claims and equivalents thereof.

The embodiments of the invention in which an exclusive property or privilege is claimed are defined as follows:

1. A method of regulating oxidative stress in an animal host, comprising the step of administering to said host an antioxidatively effective amount of a 4-thiohistidine compound of the formula:

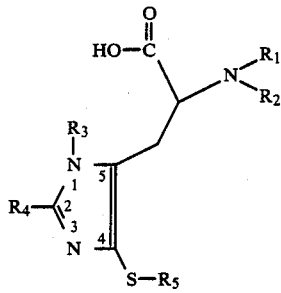

wherein $R_1$, $R_2$, $R_3$ and $R_4$ are individually selected from hydrogen and methyl, and $R_5$ is hydrogen or a 4-thiohistidine.

2. The method of claim 1 wherein the compound administered to the host is ovothiol A.

3. The method of claim 1 wherein the compound administered to the host is ovothiol B.

4. The method of claim 1 wherein the compound is ovothiol C.

* * * * *

UNITED STATES PATENT AND TRADEMARK OFFICE
CERTIFICATE OF CORRECTION

PATENT NO. : 4,898,878

DATED : February 6, 1990

INVENTOR(S) : Shapiro et al.

It is certified that error appears in the above-identified patent and that said Letters Patent is hereby corrected as shown below: Title page, item [75], lines 2&3 delete "Rachel E. Klevit" and "Andreas Spaltenstein".

| Column | Line | |
|---|---|---|
| 1 | 41 | after equation insert equation number --[3]-- |
| 3 | 35 | "a" should be --as-- |
| 5 | 62 | "$CN^{31}$-insensitivity" should be --$CN^-$-insensitivity-- |
| 5 | 64 | "1-methyl-$N^{60}$" should be --1-methyl-$N^\alpha$-- |
| 6 | 8 | "forms;" should be --form;-- |
| 7 | 65 | "doe" should be --does-- |
| 9 | 12 | "concentration" should be --concentrations-- |
| 9 | 27 | "that" should be - the-- |
| 9 | 51 | "catalasedependent" should be --catalase-dependent-- |
| 10 | 24 | after "1" insert --to-- |
| 10 | 32 | "13 $PR_1R_2$" should be -- -$PR_1R_2$-- |
| 10 | 35&36 | "-$C(-=NA_1)NA_2A_3$" should be -- -$C(=NA_1)NA_2A_3$-- |
| 10 | 42 | "group" should be --groups-- |

UNITED STATES PATENT AND TRADEMARK OFFICE
CERTIFICATE OF CORRECTION

PATENT NO. : 4,898,878
DATED : February 6, 1990
INVENTOR(S) : Shapiro et al.

It is certified that error appears in the above-identified patent and that said Letters Patent is hereby corrected as shown below:

| Column | Line | |
|---|---|---|
| 11 | 32 | "substituents" should be --substituent-- |
| 11 | 37 | "C-4positioning" should be --C-4 positioning-- |
| 12 | 9 | "animals" should be --animal-- |
| 12 | 25 | "perservatives" should be --preservatives-- |
| 14 | 9 & 10 | "Specimans" should be --Specimens-- |
| 14 | 29 | "concetration" should be --concentration-- |
| 16 | 2 | "superatant" should be --supernatant-- |
| 16 | 11 | "$\leq 100,000$" should be -->100,000-- |
| 17 | 29 | "$C^{60}H$" should be --$C^{\alpha}H$-- |
| 17 | 44 | "$C^{60}H$" should be --$C^{\alpha}H$-- |
| 18 | 6 | "C(Turner et al., 1986)" should be --C (Turner et al., 1986)-- |
| 18 | 40 | "peak C." should be --peak c.-- |

UNITED STATES PATENT AND TRADEMARK OFFICE
CERTIFICATE OF CORRECTION

PATENT NO. : 4,898,878
DATED : February 6, 1990
INVENTOR(S) : Shapiro et al.

It is certified that error appears in the above-identified patent and that said Letters Patent is hereby corrected as shown below:

| Column | Line | |
|---|---|---|
| 18 | 48 | "N-3(see below)" should be --N-3 (see below)-- |
| 18 | 58 | "0.1α1.0" should be --0.1-1.0-- |
| 19 | 38&39 | "25° C" (separate lines) should be --25°C-- (together) |
| 21 | 15 | "sterospecificity" should be --stereospecificity-- |
| 21 | 20 | "disteroisomer" should be --distereoisomer-- |
| 21 | 36 | "C(8)" should be --C (8)-- |
| 22 | 46&47 | "$NR_2^1$" should be --$NR_2^1$-- |
| 26 | 28 | "active" should be --activate-- |
| 27 | 18 | "propogates" should be --propagates-- |
| 28 | 67 | "no" should be --not-- |
| 29 | 1 | "above described" should be --above-described-- |
| 29 | 29 | "hemoglogin" should be --hemoglobin-- |
| 29 | 40 | "hemoglogin" should be --hemoglobin-- |

Signed and Sealed this

Ninth Day of July, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,898,878
DATED : February 6, 1990
INVENTOR(S) : Shapiro et al.

It is certified that error appears in the above-identified patent and that said Letters Patent is hereby corrected as shown below:

Column 1, line 3, before "Technical Field," insert:

--This invention was made with government support under grant number GM238910 awarded by the National Institutes of Health. The government has certain rights in the invention.--

Signed and Sealed this

Sixth Day of July, 1993

*Attest:*

MICHAEL K. KIRK

*Attesting Officer*   *Acting Commissioner of Patents and Trademarks*